(12) United States Patent
Kumar et al.

(10) Patent No.: US 7,612,166 B2
(45) Date of Patent: Nov. 3, 2009

(54) FLUOROUS CAPPING REAGENTS AND METHODS FOR PEPTIDE PURIFICATION

(75) Inventors: Krishna Kumar, Cambridge, MA (US); Vittorio Montanari, Somerville, MA (US)

(73) Assignee: Trustees of Tufts College, Boston, MA (US)

( * ) Notice: Subject to any disclaimer, the term of this patent is extended or adjusted under 35 U.S.C. 154(b) by 0 days.

(21) Appl. No.: 11/597,067

(22) PCT Filed: May 18, 2005

(86) PCT No.: PCT/US2005/017507

§ 371 (c)(1),
(2), (4) Date: Apr. 24, 2008

(87) PCT Pub. No.: WO2005/118527

PCT Pub. Date: Dec. 15, 2005

(65) Prior Publication Data

US 2008/0275216 A1    Nov. 6, 2008

Related U.S. Application Data

(60) Provisional application No. 60/573,105, filed on May 21, 2004.

(51) Int. Cl.
*A61K 38/00* (2006.01)
*C07K 1/00* (2006.01)

(52) U.S. Cl. ............... 530/344; 536/127; 536/25.4; 558/61; 570/141

(58) Field of Classification Search ............ 428/195; 564/305; 568/56; 570/181
See application file for complete search history.

(56) References Cited

U.S. PATENT DOCUMENTS

| 5,777,121 A | 7/1998 | Curran et al. |
|---|---|---|
| 5,859,247 A | 1/1999 | Curran et al. |
| 6,156,896 A | 12/2000 | Curran et al. |
| 6,794,492 B2 * | 9/2004 | DesMarteau et al. ........ 530/331 |
| 2002/0015826 A1 * | 2/2002 | Desmarteau et al. ........ 428/195 |

OTHER PUBLICATIONS

Zhang et al., Direct methylation and trifluoroethylation of imidazole and pyridine derivatives, Chemical Communications (Cambridge, United Kingdom) (2003), (18), 2334-2335.*
DesMarteau et al., Easy preparation of bioactive peptides from the novel Na-trifluoroethyl amino acids, Chemistry Letters (2000), (9), 1052-1053.*
DesMarteau et al., The first fluoroalkylation of amino acids and peptides in water utilizing the novel iodonium salt CF3SO2)2NI(Ph)CH2CF3, Chemical Communications (Cambridge) (1998), (20), 2241-2242.*

* cited by examiner

*Primary Examiner*—Daniel M Sullivan
*Assistant Examiner*—Chukwuma O Nwaonicha
(74) *Attorney, Agent, or Firm*—Foley Hoag LLP

(57) ABSTRACT

Aspects of the present invention relate to compounds for preparing fluorocarbon compounds, methods for preparing fluorocarbon compounds, and methods for purifying a mixture of compounds. One aspect of the present invention relates to a trivalent iodonium fluorocarbon. The trivalent iodonium fluorocarbon compound of the invention is useful for attaching a fluorocarbon group to a compound that has a nucleophilic functional group. Another aspect of the present invention relates to a method of preparing a trivalent iodonium fluorocarbon. Another aspect of the present invention relates to a method of preparing a fluorocarbon by treating a compound bearing a nucleophilic functional group with a trivalent iodonium fluorocarbon compound. Another aspect of the present invention relates to a method or purifying a mixture comprising a first and a second compound by treating the mixture with a trivalent iodonium fluorocarbon to attach a fluorocarbon group to the second compound leaving the first compound unchanged, and purifying the mixture by fluorous-phase purification.

22 Claims, 4 Drawing Sheets

Crude peptide mixture

○ Fluorous tagged deletion products
● Desired full length peptide

Flourous flash filtration

Pure full length peptide product

FLUOROUS CAPPING REAGENTS AND METHODS FOR PEPTIDE PURIFICATION

RELATED APPLICATIONS

This application claims the benefit of priority to Patent Cooperation Treaty Application number PCT/US2005/017507, filed May 18, 2005; which claims the benefit of priority to U.S. Provisional Patent Application Ser. No. 60/573,105, filed May 21, 2004.

GOVERNMENT SUPPORT

This invention was made with support provided by the National Institutes of Health (Grant No. GM65500) and the National Science Foundation (Grant No. CHE-0236846); therefore, the government has certain rights in the invention.

BACKGROUND OF THE INVENTION

Solid-phase peptide synthesis (SPPS) has become a mainstay method for the synthesis of small to medium length peptides and proteins. Peptides of substantially longer length can be prepared using SPPS methods owing to the advent of native chemical ligation methods. See Merrifield, R. B. *J. Am. Chem. Soc.* 1963, 85, 2149 and Dawson, P. E.; Muir, T. W.; Clarklewis, I.; Kent, S. B. H. *Science* 1994, 266, 776-779. However, removal of deletion sequences, that often accumulate during synthesis, from the desired full-length product remains a tedious, undesirable aspect of SPPS. A similar problem has also been noted in the solid-phase synthesis of oligosaccharides. See P. H. Seeberger et al. *Angew. Chem. Int. Ed.* 2001, 40, 4433 and U.S. Patent Application 2003/0232978. In particular, removal of sequences, e.g., peptide or oligosaccharide sequences, differing by only one unit (so-called "n–1 products"), which stem from incomplete conversion at any stage of the synthesis, can be very difficult. In response to the need for better purification procedures, a number of methods have been reported for the isolation and purification of biopolymers, including biopolymers produced by chemical synthesis or recombinant DNA techniques. For example, centrifugation, column chromatography, and electrophoresis can be used to purify biopolymers. Unfortunately, these methods require one or more additional and often burdensome purification steps after initial purification of the biopolymer. These purification procedures are also unsatisfactory because a significant amount of the crude biopolymer is often lost during the procedure resulting in reduced yields.

To facilitate purification of peptides and proteins prepared by SPPS, various reagents have been developed with the intention of tagging deletion sequences or the full-length product. The compound bearing the tag has different chemical properties and can be separated from other compounds using various purification methods, e.g., chromatographic purification. Several chemical groups that function as purification handles have been described that take advantage of selective conditions under which the retention time can be varied on ion-exchange, hydrophobic interaction, affinity and other types of chromatographic columns. See Funakoshi, S.; Fukuda, H.; Fujii, N., *J. Chromatogr.* 1993, 638, 21-27; Shogren-Knaak, M. A.; McDonnell, K. A.; Imperiali, B., *Tetrahedron Lett.* 2000, 41, 827-829; Shogren-Knaak, M. A.; Imperiali, B. *Tetrahedron Lett.* 1998, 39, 8241-8244; Villain, M.; Vizzavona, J.; Rose, K. *Chem. Biol.* 2001, 8, 673-679; Vizzavona, J.; Villain, M.; Rose, K. *Tetrahedron Lett.* 2002, 43, 8693-8696; Canne, L. E.; Winston, R. L.; Kent, S. B. H. *Tetrahedron Lett.* 1997, 38, 3361-3364; and P. C. de Visser et al. *Tetrahedron Lett.* 2003, 9013. Nevertheless, purification of peptides remains a difficult task, particularly purification of peptide sequences differing by only one residue (n–1 products). For additional discussion relating to solid-phase peptide synthesis see Cotton, G. J.; Muir, T. W. *Chem. Biol.* 1999, 6, R247-R256; Canne, L. E.; Botti, P.; Simon, R. J.; Chen, Y. J.; Dennis, E. A.; Kent, S. B. H. *J. Am. Chem. Soc.* 1999, 121, 8720-8727; Dawson, P. E.; Kent, S. B. H. *Annu. Rev. Biochem.* 2000, 69, 923-960; and Kochendoerfer, G. G.; Kent, S. B. H. *Curr. Opin. Chem. Biol.* 1999, 3, 665-671.

Fluorous-phase purification is an attractive technique for the purification of peptides, oligosaccharides, oligonucleotides, and small organic compounds. In fluorous purification procedures, prior to purification a group containing a relatively large number of fluorine atoms is attached to the compound to be purified. The step of attaching the fluorous group to the compound imparts unique chemical properties to the compound, thereby making it easier to separate the fluoro-tagged compound from other compounds. In general, fluorous-tagged molecules partition preferentially into a fluorous phase while non-tagged molecules partition into an organic phase. The fluorous tag can be installed while the compound is attached to the solid phase or the fluorous tag can be installed using solution-phase chemistry. Recently, highly-fluorinated compounds have been employed in protein design, reaction acceleration catalysis, combinatorial chemistry, and organic separation methodology. Among the canonical amino acid side chain functionalities, none are expected to extensively interact with fluorous materials. Thus, an appendage that is highly fluorinated should be unique in its physical properties, compared to most peptide products. See Filippov, D. V.; van Zoelen, D. J.; Oldfield, S. P.; van der Marel, G. A.; Overkleeft, H. S.; Drijfhout, J. W.; van Boom, J. H. *Tetrahedron Lett.* 2002, 43, 7809-7812. Although fluorous synthetic and/or separation techniques are promising, such techniques are currently limited by a lack of available and suitable fluorinated compounds that can be used to install fluorinated molecular tags.

Therefore, the need exists for fluorinated compounds that can be used to install fluorinated molecular tags and methods of purification using the fluorinated molecular tags. The present invention fulfills this need and has other related advantages.

SUMMARY OF THE INVENTION

The present invention generally relates to compounds for preparing fluorocarbon compounds, methods for preparing fluorocarbon compounds, and methods for purifying a mixture of compounds. One aspect of the present invention relates to a trivalent iodonium fluorocarbon. The trivalent iodonium fluorocarbon compound of the invention is useful for attaching a fluorocarbon group to a compound that has a nucleophilic functional group. In a preferred embodiment, the trivalent iodonium fluorocarbon is the triflimide salt of pentadecafluorooctyliodonium benzene. Another aspect of the present invention relates to a method of preparing a trivalent iodonium fluorocarbon. In a preferred embodiment, the trivalent iodonium fluorocarbon is prepared by admixing a triflimide and a iodo-fluoroalkane in the presence of benzene. Another aspect of the present invention relates to a method of preparing a fluorocarbon by treating a compound bearing a nucleophilic functional group with a trivalent iodonium fluorocarbon compound. In a preferred embodiment, the nucleophilic functional group is an amine. Another aspect of the present invention relates to a method of purifying a mixture comprising a first and a second compound by treating the mixture with a trivalent iodonium fluorocarbon to attach a fluorocarbon group to the second compound leaving the first compound unchanged, and purifying the mixture by fluorous-phase purification. In a preferred embodiment, the purification is fluorous chromatography.

DETAILED DESCRIPTION OF THE INVENTION

Overview

Figure 1:
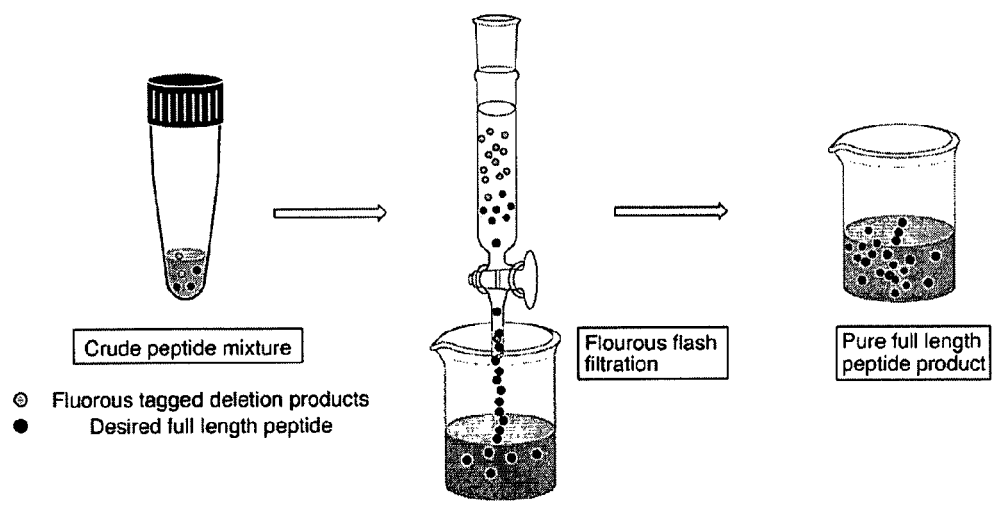
FIG. 1 depicts schematically purification aided by fluorous tagging.

The present invention generally relates to fluorinated compounds and methods of purifying fluorinated compounds. The compounds and methods of the invention are useful in the purification of peptides, oligosaccharides, oligonucleotides, and small organic compounds. One aspect of the present invention relates to a trivalent iodonium fluorocarbon that can be used to attach fluorocarbon groups to another molecule bearing a nucleophilic functional group. Another aspect of the present invention relates to a method of preparing a trivalent iodonium fluorocarbon. In a preferred embodiment, the trivalent iodonium fluorocarbon is prepared by admixing a triflimide and an iodo-fluoroalkane in the presence of benzene. Another aspect of the present invention relates to a method of preparing fluorinated compounds comprising reacting a trivalent iodonium fluorocarbon with a compound bearing a nucleophilic functional group. The nucleophilic functional group can be hydroxyl, amino, thio, seleno, alkoxide, amide, thiolate, selenate, phosphine, or a carbon nucleophile, such as a ketone, ester, amide, silylenolether, malonate, β-ketoester, α-nitroester, α-cyanoester, α-phosphonoester, or α-ketophosphonate. In a preferred embodiment, the nucleophilic functional group is a primary amine. Another aspect of the present invention relates to a method of purifying a compound by reacting a mixture of the desired compound and impurities with the a trivalent iodonium fluorocarbon which converts selectively the impurities to fluorocarbon-tagged compounds, and then the mixture is purified to isolate the non-fluorous-tagged compound. Alternatively, a compound that is part of a mixture with one or more compounds can be purified by reacting the compound to be purified with a trivalent iodonium fluorocarbon to form a fluorocarbon-tagged compound and then purifying the fluorocarbon-tagged compound to separate it from the impurities.

A large number of fluorous-phase purification techniques are known in the art and are amenable to the present invention. Examples of fluorous-phase purification techniques include silica gel chromatography using fluorous silica gel (e.g., column chromatography and high performance liquid chromatography), liquid-liquid extraction using a fluorocarbon solvent and a non-fluorocarbon solvent, and liquid-solid extraction using a fluorocarbon solvent.

The purification procedures of the invention can be used to isolate peptides in high chemical purity. As described above, peptides are usually synthesized on solid support using automated techniques. Automated peptide synthesizers typically use a capping step to terminate chains resulting from incomplete coupling steps. In order to facilitate removal of chains resulting from incomplete coupling steps, the capping reagent generally has chemical properties that are orthogonal to the properties of other protection groups on the peptide. However, removal of peptide chains produced from incomplete coupling steps is often very difficult.

SOME PREFERRED EMBODIMENTS

In response to the need for a capping agent in peptide synthesis that would allow for facile purification of the desired product, we have developed trivalent iodonium fluorocarbon compounds. The following design elements were central to the development of the capping reagent. First, the reagent should react readily with free amines of α-amino acids to deliver a fluoroalkyl chain. Second, the reactivity of the amine should be substantially reduced upon capping so that the amine does not react appreciably in further peptide coupling steps. Finally, the tag should be stable to subsequent peptide coupling reactions. The trivalent iodonium fluorocarbon compound of the invention possesses all these relevant properties, and functions as a useful tag for t-Boc-based SPPS. Furthermore, the trivalent iodonium fluorocarbon compound of the invention is compatible with the solvent systems of peptide synthesis, and is efficient at tagging free amines with an fluorocarbon group, e.g., $-(CH_2)C_7F_{15}$ or $-(CH_2)C_9F_{19}$. Once the free amines have been capped with the fluorocarbon fragment, they are unreactive in further peptide coupling steps and are stable to both deprotection in neat trifluoroacetic acid, and to the final cleavage step in anhydrous HF. For other fluorocarbon transfer reagents that have been used predominately in aqueous solutions, see: DesMarteau, D. D.; Montanari, V. *Chem. Commun.* 1998, 2241-2242; DesMarteau, D. D.; Montanari, V. *Chem. Lett.* 2000, 1052-1053; and D. D. DesMarteau et al. *J. Fluor. Chem.* 2003, 122, 57-61. In a preferred embodiment, the trivalent iodonium fluorocarbon of the invention is compound 1a or 1b represented below.

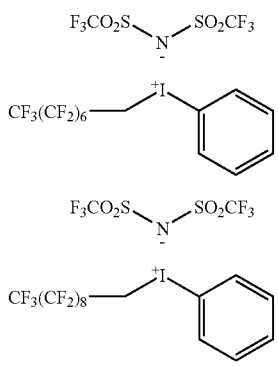

1a

1b

The reactivity of the trivalent iodonium fluorocarbon compounds can be tuned to optimize their yields in reactions with specific substrates. For example, either one or both of the trifluorosulfonyl groups can be replaced with a more powerful electron-withdrawing group or a group that is less electron-withdrawing. The trifluorosulfonyl group can be replaced by an alkyl or aryl ester, alkyl or aryl amide, acyl, or an aryl group optionally substituted with a nitro, cyano, halogen, ester, amide, or acyl group. In certain instances, the trifluorosulfonyl group is replaced with a trifluoroacetate group. In certain instances, the trifluorosulfonyl group is replaced with an alkyl, aryl, aralkyl, or alkenyl group. In certain instances, the aromatic group bonded to the iodide is substituted by halogen, alkoxyl, dialkylamine, acyl, amide, ester, nitro, or cyano. In certain instances, the phenyl group bonded to the iodide is replaced with an alkene. In certain instances, the alkene is substituted with halogen, alkoxyl, dialkylamine, acyl, amide, ester, nitro, or cyano.

The functional groups of trivalent iodonium fluorocarbon 1a and 1b have been selected so that the reactivity of compounds 1a and 1b are compatible with peptide synthesis. See Zhdankin, V. V.; Stang, P. J., Chem. Rev. 2002, 102, 2523-2584. For example, reaction of two equivalents of compound 1a with the t-butyl carboxyl ester of tyrosine 2 in the presence of collidine/CH$_2$Cl$_2$ resulted in quantitative monoalkylation of the amino group in no more than 10 minutes to give 3a (after reaction with ClCOOEt, H$_2$O/THF, and Na$_2$CO$_3$). The purified alkylated product did not react further when treated with reagent 1a for an additional 30 minutes under identical conditions. Likewise, for example, reaction of one equivalent of compound 1b with the t-butyl carboxyl ester of tyrosine 2 in the presence of collidine/CH$_2$Cl$_2$ resulted in monoalkylation of the amino group in 80% yield to give 3b (after reaction with ClCOOEt, H$_2$O/THF, and Na$_2$CO$_3$). As was true for 2b, the purified alkylated product 3b did not react further when treated with reagent 1b under identical conditions.

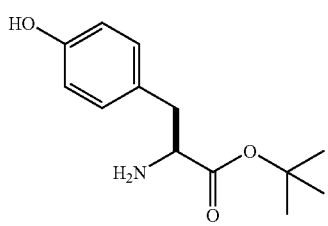

2

-continued

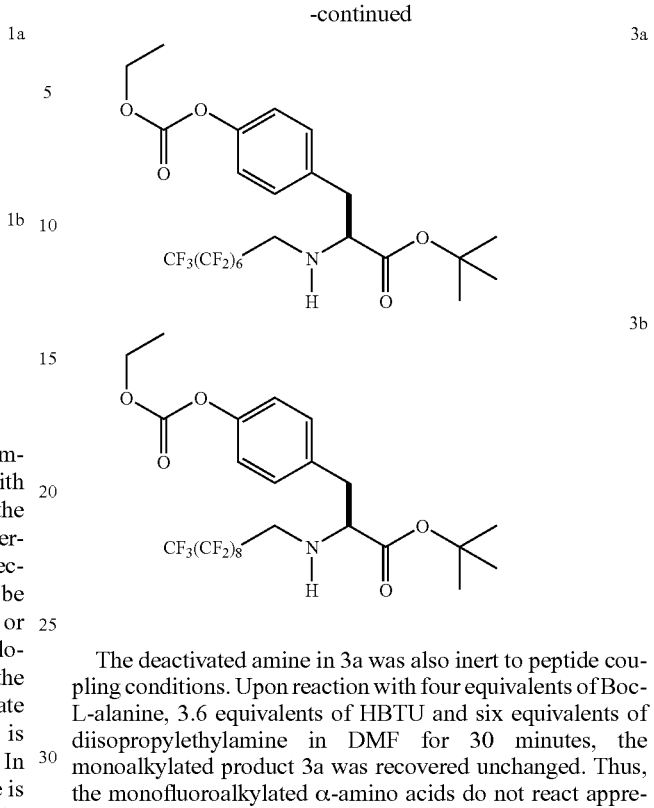

3a

3b

The deactivated amine in 3a was also inert to peptide coupling conditions. Upon reaction with four equivalents of Boc-L-alanine, 3.6 equivalents of HBTU and six equivalents of diisopropylethylamine in DMF for 30 minutes, the monoalkylated product 3a was recovered unchanged. Thus, the monofluoroalkylated α-amino acids do not react appreciably in subsequent reactions encountered during standard peptide synthesis reactions using t-Boc chemistry.

In addition, as a control experiment, F-alkylated compound 5 was prepared (from 4 TFA/CH$_2$Cl$_2$, followed by treatment excess 0.5 M NaHCO$_3$/CH$_2$Cl$_2$ and subsequent treatment with 1 eq. 1a) and stirred in pyridine/DMF for 20 hours at 20° C.; 5 was recovered in 91% yield after workup and chromatography.

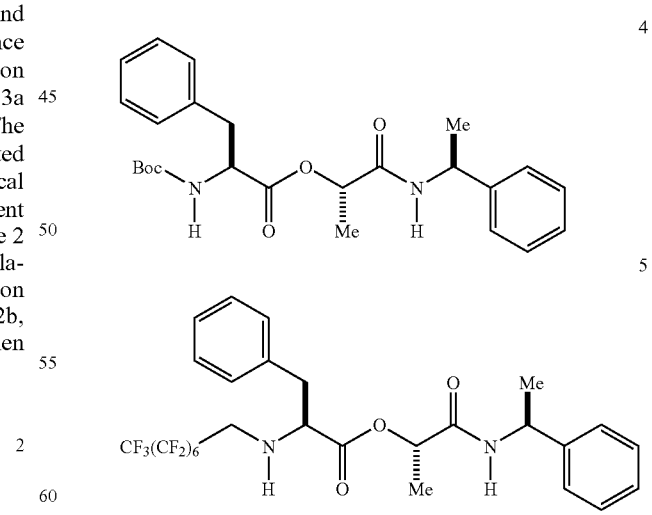

4

5

To demonstrate the versatility and utility of the trivalent iodonium fluorocarbon compound of the invention, reagent 1a was employed in capping amines from intentionally incomplete couplings during SPPS. This test was used on peptides of length 10 (P1), 21 (P2) and 14 residues (P3), which are variants of the acyl carrier peptide 65-74 (ACP 65-74), adrenocorticotropic hormone 18-39 and insulin-like growth factor 28-41 (IGF 28-41) respectively. The structure of P1, P2 and P3 are as follows:

(P1) Ac-NH-VEA*AID*YI*DA-CONH$_2$;
(P2) Ac-NH-RAV*KYV*ADAA*EDESAEAFALEF-CONH$_2$;
(P3) Ac-NH-PT*GYGS*SSRRAPET-CONH$_2$.

Positions where peptide coupling was intentionally incomplete are marked with an asterisk. Peptides were synthesized using the in-situ neutralization protocol using t-Boc chemistry on MBHA (methylbenzhydrylamine) resin. See M. Schnolzer et al. *Int. J. Pept. Protein Res.* 1992, 40, 180-193. To assure incomplete coupling at selected sites, 0.8 equivalents of amino acid and 0.72 equivalent HBTU were used, and the reaction was allowed to proceed for 20 minutes. This step was followed by a one-minute flow wash with DMF. The resin was then washed thoroughly with CH$_2$Cl$_2$ using a combination of shake and flow washes. The capping step was performed with a solution containing two equivalents of 1a in CH$_2$Cl$_2$ with collidine as a base for 15 minutes and was repeated once with one equivalent of 1a (Scheme 1). The resin was thoroughly washed with CH$_2$Cl$_2$ and the cycle of deprotection and coupling steps was then resumed in a normal manner. Capping steps were performed only at sites where couplings were incomplete.

Scheme 1

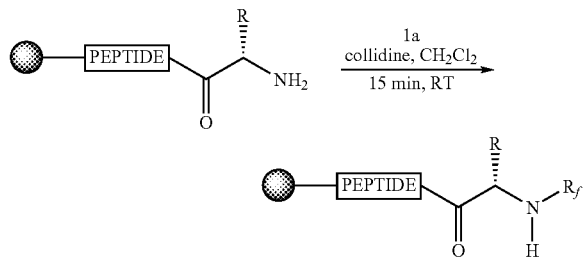

The capped peptides were removed in one of two ways. In the case of the smaller peptide P1, the crude product obtained from the cleavage reaction was simply dissolved in 1% AcOH solution and centrifuged at 14,000 rpm for 10 minutes. This method produced a pellet of material capped with the fluorous tag. Analysis of the precipitate by ESI-MS after redissolution in MeOH/H$_2$O indicated it was predominantly a mixture of the monofluoroalkylated products. The supernatant was injected after further acidification with 0.1% trifluoroacetic acid (TFA) on a Vydac C18 reverse phase column and eluted with a gradient of CH$_3$CN in water (0.1% TFA). The results with the smaller peptide P1 are displayed in FIG. 2 part a. When the capping was carried out with 1a, after centrifugation, all deletion sequences precipitate leaving only the full-length product in solution. While plain addition of water followed by centrifugation was enough for removal of small peptides (8-10 residues in length) which were fluoroalkylated, longer tagged-peptides needed passage through fluorous flash silica gel in aqueous solvents to be efficiently excluded.

Figure 2:
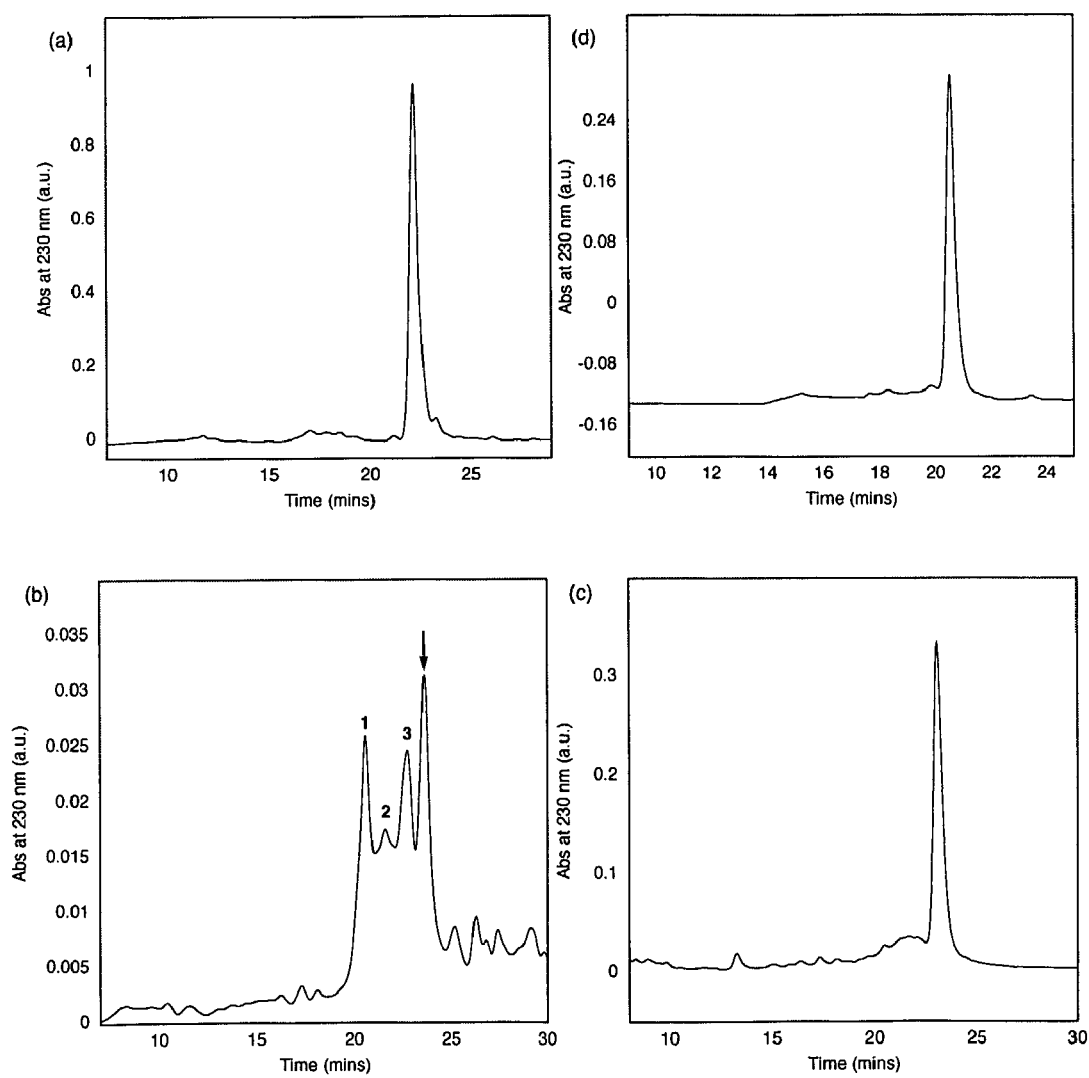
FIG. 2 depicts the results from purification aided by fluorous tagging with 1a. Note: (a) depicts reversed-phase HPLC chromatogram (Vydac C18) of ACP analogue P1 synthesized using incomplete couplings at positions marked by asterisks in the sequence, and capping with 1a, wherein the crude product was dissolved in 1% AcOH and centrifuged and the supernatant injected; (b) depicts a chromatogram of peptide P2 synthesized using $Ac_2O$ capping (full-length product is marked with an arrow and peaks 1, 2 and 3 are acetylated products of increasing mass); (c) depicts peptide P2 synthesized using fluorous capping; (d) depicts a chromatogram of P3 obtained from synthesis employing capping reagent 1a. Samples in (b), (c) and (d) were subjected to filtration through fluorous silica gel prior to HPLC analysis.

The chromatogram obtained from the synthesis of P2 with Ac$_2$O as the capping reagent is shown in FIG. 2 part b, while FIG. 2 part c shows the same synthesis carried out with 1a as the capping reagent. Both samples were subject to fluorous flash silica filtration using CH$_3$CN:H$_2$O (1:4, 1% AcOH) solvent. In the case of the products tagged with 1a, all the fluorous material is retained on the column leaving mostly the desired full-length product, while the acetic anhydride capped products closely mirror the elution profile of the final product. A short filtration removes almost all the deletion products generated during the synthesis of the 21-residue peptide using reagent 1, thus greatly simplifying purification. Peptide P3 gave similar results (see FIG. 2 part d). Elution solvent for the fluorous flash column in the case of peptide P3 was 1% AcOH.

Remarkably, an efficient and robust genus of fluorous tagging reagents has been invented that facilitate the preparation and purification of routine and difficult peptide and protein sequences using BOC-protected amino acids. However since a majority of automated synthesizers work using Fmoc chemistry, a modified protocol incorporating a fluorous capping step as a routine procedure would be desirable. The capping reagents of the present invention are amenable to such a modified protocol, as described below.

Figure 3:
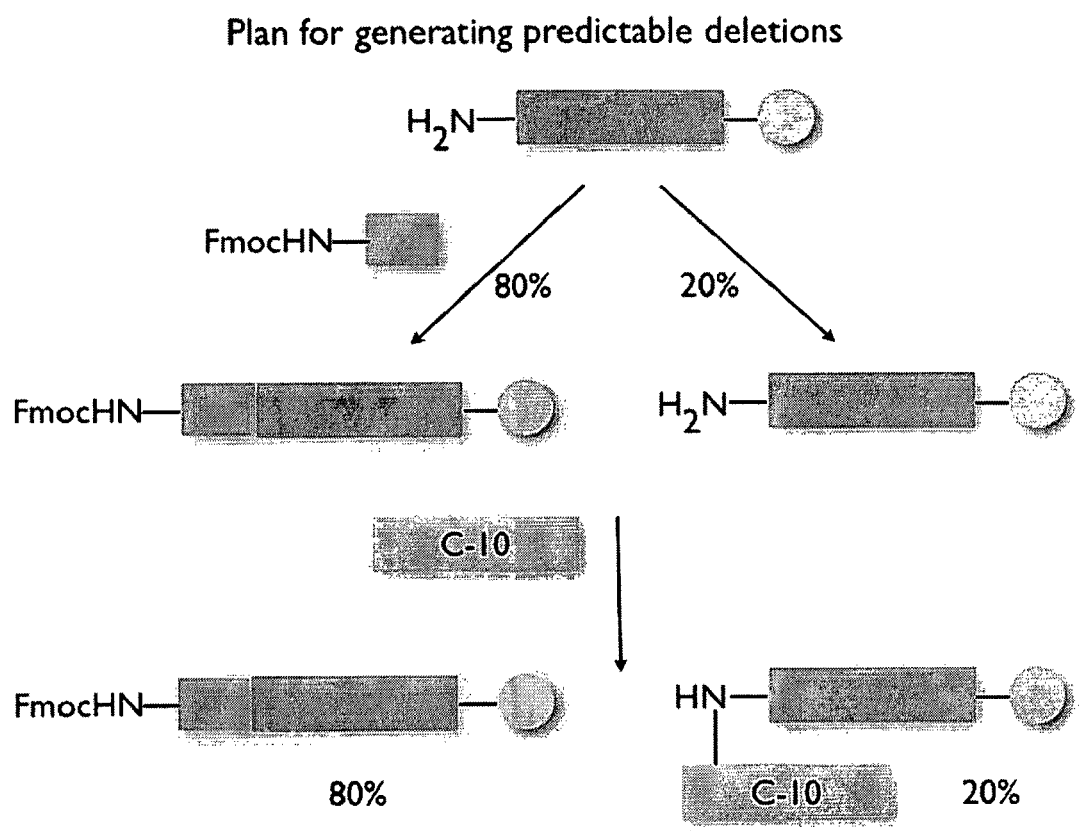
FIG. 3 depicts a plan for generating predictable deletions with Fmoc protected peptides. "C-10" denotes $-CH_2(CF_2)_8CF_3$.

The use of 1a and 1b in manually operated Fmoc peptide syntheses, capping intentional deletions, was investigated. Since the percentage of incomplete coupling using less than 1 eq. Fmoc-amino acid was found to be widely variable (results not shown), and usually unrealistically large, compared to similar experiments in Boc-chemistry described above, intentional deletions were instead generated in a consistent manner by withdrawing 20% wt of the resin at the desired positions (FIG. 3). The model peptides used were P4, P5 and P6 which are analogs of ACP 65-74, IGF 28-41, and Bombesin 5-14, respectively. The structures of P4, P5 and P6 are shown below:

(P4) Ac-NH-V*EAAIDYIDA-CONH$_2$;
(P5) Ac-NH-PT*GY*GSSSRRAPET-CONH$_2$;
(P6) Ac-NH-GN*QW*AVGHLC-CONH$_2$.

Figure 4:
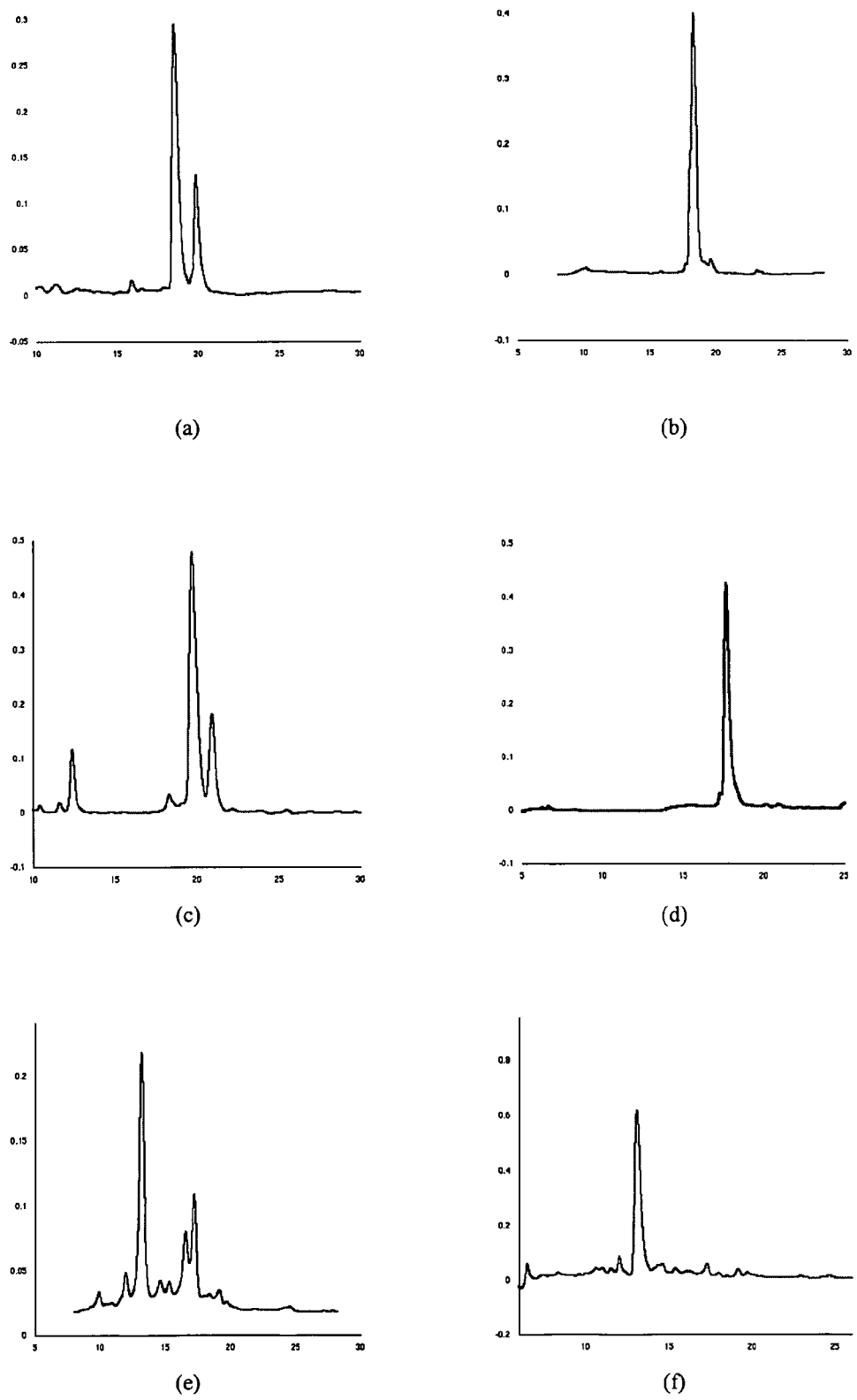
FIG. 4 depicts the results from purification aided by fluorous tagging with 1b. Note: (a) depicts a reversed-phase HPLC chromatogram (Vydac C18) of P4 (automated synthesis); (b) depicts a reversed-phase HPLC chromatogram (Vydac C18) of P4 (automated synthesis) wherein the acetyl group is replaced with $-CH_2(CF_2)_8CF_3$; (c) depicts a reversed-phase HPLC chromatogram (Vydac C18) of P5 (automated synthesis); (d) depicts a reversed-phase HPLC chromatogram (Vydac C18) of P5 (automated synthesis) wherein the acetyl group is replaced with $-CH_2(CF_2)_8CF_3$; (e) depicts a reversed-phase HPLC chromatogram (Vydac C18) of P6 (manual synthesis); and (f) depicts a reversed-phase HPLC chromatogram (Vydac C18) of P6 (manual synthesis) wherein the acetyl group is replaced with $-CH_2(CF_2)_8CF_3$

Successful fluorous capping by automated synthesis of P4 and P5 was demonstrated. In addition, P6 was capped by a protocol that consists of soaking the resin with an iodonium salt solution, then draining and recovering this solution and finally adding a base ("manual synthesis). In this manner the solution of iodonium salt can be recycled several times. Because the salt and the base are employed separately, other bases besides collidine may be used in this protocol. The results are shown in FIG. 4.

As explained above, it was determined that the R$_f$CH$_2$NH— residue is a stable tag under repeated treatment with piperidine in DMF, and that the acid-labile side chain protections are stable to repeated use of 1a and 1b. However, the only found incompatibility was with the uncommon amino acid methionine. Interestingly, S-trityl cysteine is compatible with the invention.

In addition, the fluorocarbon transfer reagents of the invention are also useful in preparation of fluorinated compounds which are important components used in protein design, reaction acceleration, catalysis, combinatorial chemistry, and organic separation methods. See Bilgicer, B.; Kumar, K. *J. Chem. Educ.* 2003, 80, 1275-1281; Yoder, N. C.; Kumar, K. *Chem. Soc. Rev.* 2002, 31, 335-341; Bilgicer, B.; Kumar, K. *Tetrahedron* 2002, 58, 4105-4112; Bilgicer, B.; Xing, X.; Kumar, K. *J. Am. Chem. Soc.* 2001, 123, 11815-11816; Bilgicer, B.; Fichera, A.; Kumar, K. *J. Am. Chem. Soc.* 2001, 123, 4393-4399; Tang, Y.; Tirrell, D. A. *J. Am. Chem. Soc.* 2001, 123, 11089-11090; Wang, P.; Tang, Y.; Tirrell, D. A., *J. Am. Chem. Soc.* 2003, 125, 6900-6906; Tang, Y.; Ghirlanda, G.; Petka, W. A.; Nakajima, T.; DeGrado, W. F.; Tirrell, D. A. *Angew. Chem. Int. Edit.* 2001, 40, 1494; Tang, Y.; Ghirlanda, G.; Vaidehi, N.; Kua, J.; Mainz, D. T.; Goddard, W. A.; DeGrado, W. F.; Tirrell, D. A., *Biochemistry* 2001, 40, 2790-2796; Myers, K. E.; Kumar, K. *J. Am. Chem. Soc.* 2000, 122, 12025-12026; Jenner, G.; Gacem, B., *J. Phys. Org. Chem.* 2003, 16, 265-270; Gladysz, J. A., *Chem. Rev.* 2002, 102, 3215-3216; Gladysz, J. A.; Curran, D. P. *Tetrahedron* 2002, 58, 3823-3825; Wende, M.; Gladysz, J. A., *J. Am. Chem. Soc.* 2003, 125, 5861-5872; Curran, D. P.; Luo, Z. Y. *J. Am. Chem. Soc.* 1999, 121, 9069-9072; Luo, Z. Y.; Zhang, Q. S.; Oderaotoshi, Y.; Curran, D. P. *Science* 2001, 291, 1766-1769; and Palmacci, E. R.; Hewitt, M. C.; Seeberger, P. H., *Angew. Chem. Int. Edit.* 2001, 40, 4433.

Fluorous Phase Separation Methods

Separation of the fluorous-tagged compounds of the present invention is achieved using fluorous separation techniques that are based upon differences in chemical properties between fluorinated and non-fluorinated compounds. The term "fluorous separation technique" refers generally to a method that is used to separate mixtures containing fluorous molecules or organic molecules bearing fluorous domains or tags from each other and/or from non-fluorous compounds based predominantly on differences in the fluorous nature of molecules; for example, size and/or structure of a fluorous molecule or domain or the absence thereof. Fluorous separation techniques include fluorous liquid-liquid extraction, fluorous solid phase extraction, and fluorous chromatography. See, for example, Danielson, N. D. et al., "Fluoropolymers and Fluorocarbon Bonded Phases as Column Packings for Liquid Chromatography," *J. Chromat.* 1991, 544, 187-199; Curran, D. P. "Fluorous Reverse Phase Silica Gel. A New Tool for Preparative Separations in Synthetic Organic and Organofluorine Chemistry," *Synlett*, 2001, 9, 1488; Curran D. P., "Fluorous Techniques for the Synthesis of Organic Molecules: A Unified Strategy for Reaction and Separation." In: Stimulating Concepts in Chemistry (M. Shibasaki, J. Fraser Stoddart and F. Vogtle, eds.), Wiley-VCH, Weinheim, 2000, 25. Examples of suitable fluorocarbon bonded phases include FluoroFlash® columns commercially available from Fluorous Technologies Inc. (Pittsburgh, Pa.), Fluofix® and Fluophase® columns commercially available from Keystone Scientific, Inc. (Bellefonte, Pa.), and FluoroSep™-RP-Octyl commercially available from ES Industries (Berlin, N.J.). Other fluorous separation techniques suitable for the present invention include liquid-liquid based separation methods, such as liquid-liquid extraction or countercurrent distribution with a fluorous solvent and an organic solvent. Several fluorous reaction and separation techniques are disclosed, for example, in U.S. Pat. Nos. 6,156,896; 5,859,247 and 5,777,121, the disclosures of which are incorporated by reference. In addition, several fluorous reaction and separation techniques are disclosed in U.S. patent application Ser. No. 09/506,779; Ser. No. 09/565,087; Ser. No. 09/583,247; Ser. No. 09/932,903; Ser. No. 09/977,944 and Ser. No. 10/094,345, the disclosures of which are incorporated by reference.

The following is a general procedure for liquid-liquid extraction of a fluorocarbon compound. The fluorocarbon compound to be purified is dissolved in MeCN and extracting 1-5 times with FC-72. FC-72 is a fluorocarbon solvent commercially available (3M) which includes perfluorohexane ($C_6F_{14}$) isomers (bp 56° C.). Concentration of the fluorous extracts yields the fluorous product. After this extraction, generally only minor amounts of the fluorous product remain in the MeCN layer.

The following is a general procedure for column chromatographic purification of a mixture containing fluorocarbon-tagged compounds and compounds lacking a fluorocarbon tag. In certain instances, such as purification of peptide deletion sequences, the impurities are labeled with a fluorous group while the desired compound does not have a fluorous group. In such instances, a mixture of fluorous-tagged impurities and non-fluorous-tagged compound is loaded onto the column packed with fluorous-phase silica gel. The column is eluted with solvent such that the non-fluorinated compound proceeds rapidly though the fluorous-phase silica gel while the fluorocarbon-tagged impurities proceed very slowly through the fluorous-phase silica gel. Then, the eluent from the column is collected during the time when the non-fluorocarbon-tagged compound exits the column.

In certain instances, the desired compound is labeled with a fluorous tag while the impurities do not have a fluorous tag. In such instances, the mixture of fluorocarbon-tagged compound and non-fluorous-labeled impurities is loaded onto a column packed with fluorous-phase silica gel. The column is eluted with solvent such that non-fluorinated compounds proceed rapidly though the fluorous-phase silica gel while the fluorocarbon-tagged compound proceeds very slowly through the fluorous-phase silica gel. Then, the eluent from the column is collected during the time when the fluorocarbon-tagged compound exits the column. Alternatively, the column may be eluted with a second solvent to facilitate eluation of the fluorocarbon-tagged compound once the impurities have eluted through the column.

Purification of reaction mixtures after organic synthesis is often performed using flash chromatography, which is a chromatographic technique used to separate or fractionate products of interest using pre-packed silica columns. In flash chromatography, a column often ranging in diameter from 0.5 cm to 10 cm having a length of 4 cm to 3 meters is packed with silica gel. Then compound to be purified is loaded onto one end of the silica gel column and solvent is forced through the silica gel column, usually under pressure.

Preparation of Trivalent Iodonium Fluorocarbon Compounds

The trivalent iodonium fluorocarbons of the invention are prepared by admixing a bisacetoxyiodo-perfluocarbon compound with an imide in the presence of an aromatic compound. In certain instances, the aromatic compound is benzene or an optionally substituted phenyl group. In certain instances, the aromatic group is substituted with one or more of alkyl, cycloalkyl, aryl, aralkyl, halogen, nitro, cyano, dialkylamino, or alkoxyl. In certain instances, the aromatic compound is replaced with an optionally substituted alkene. In certain instances, the alkene is substituted with one or more of alkyl, cycloalkyl, aryl, aralkyl, halogen, nitro, cyano, dialkylamino, or alkoxyl. The perfluoro group of the bisacetoxyiodo-perfluocarbon compound can be branched or linear. In certain instances, the perfluorogroup is branched. In certain instances, the branched portion of the perfluoro group contains at least one fluorine atom. In certain instances, at least one-half of the hydrogens atoms on the backbone of the perfluorogroup have been replaced with fluorine atoms. In a preferred embodiment, at least about 75% of the hydrogens atoms on the backbone of the perfluorogroup have been replaced with fluorine atoms. In a more preferred embodiment, at least about 85% of the hydrogens atoms on the backbone of the perfluorogroup have been replaced with fluorine atoms. In a most preferred embodiment, at least about 90% of the hydrogens atoms on the backbone of the perfluorogroup have been replaced with fluorine atoms. In certain instances, at least about 95% of the hydrogens atoms on the backbone of the perfluorogroup have been replaced with fluorine atoms. In certain instances, the perfluoro group may contain an ether, thioether, or alkylamino linkage. In certain instances, the perfluoro group contains 2-50 carbon atoms. In certain instances, the perfluoro group contains 2-40 carbon atoms. In certain instances, the perfluoro group contains 3-30 carbon atoms. In certain instances, the perfluoro group contains 3-20 carbon atoms. In certain instances, the perfluoro group contains 3-15 carbon atoms. In certain instances, the perfluoro group contains 5-15 carbon atoms. In certain instances, the perfluoro group contains 5-10 carbon atoms. In a preferred embodiment, the perfluoro group contains 6-10 carbon atoms. In a preferred embodiment, the perfluoro group contains 7, 8 or 9 carbon atoms. In certain instances, the reaction is conducted in the presence of a perfluoroalkane solvent. In certain instances, the perfluoroalkane solvent is perfluoropentane, perfluorohexane, or perfluoroheptane. In a preferred embodiment, the perfluoroalkane solvent is perfluorohexane. In certain instances, the reaction is performed in the presence of an alkylacid anhydride, fluoroalkylacid anhydride, arylacid anhydride, or aralkylacid anhydride. In a preferred embodiment, the reaction is performed in the presence of trifluoroacetic anhydride. The reaction can be conducted over a range of temperatures. In certain instances, the reaction is conducted at temperature in the range of about −30° C. to about 150° C. In certain instances, the reaction is conducted at temperature in the range of about 0° C. to about 90° C. In certain instances, the reaction is conducted at temperature in the range of about 10° C. to about 50° C. In a preferred embodiment, the reaction is conducted at temperature in the range of about 15° C. to about 30° C. In certain instances, the reaction is conducted in an inert atmosphere, e.g. nitrogen or argon. In certain instances, the reaction environment is anhydrous. In certain instances, the reaction mixture contains less than about 4% by weight water. In certain instances, the reaction mixture contains less than about 2% by weight water. In certain instances, the reaction mixture contains less than about 1% by weight water. A large variety of trivalent iodonium fluorocarbon compounds can be prepared using the aforementioned procedure.

Fluorous Capping Reaction of the Invention

The fluorous capping reaction of the invention is performed by treating a compound comprising a nucleophilic function group with a trivalent iodonium fluorocarbon of the invention. In certain instances, a non-nucleophilic base is added to the reaction mixture comprising the trivalent iodonium fluorocarbon. A variety of non-nucleophilic bases are known in the art and are amenable to the present invention. Representative examples of non-nucleophilic bases amenable to the present invention are pyridine, 2,4-dimethylpyridine, 2,4,6-trimethylpyridine (collidine), 2,6-di-tetrabutylpyridine, 1,8-diazabicyclo[4.3.0]non-5-ene, triethylamine, diisopropylethylamine, and dicyclohexylamine. In a preferred embodiment, the base is collidine. In general, the subject reactions are carried out in a liquid reaction medium. The reactions are conducted in an aprotic solvent. Suitable solvents include ethers, such as diethyl ether, 1,2-dimethoxyethane, diglyme, t-butyl methyl ether, tetrahydrofuran and the like; halogenated solvents, such as chloroform, dichloromethane, dichloroethane, chlorobenzene, carbon tetrachloride, and the like; aliphatic or aromatic hydrocarbon solvents, such as benzene, xylene, toluene, hexane, heptane, pentane and the like; esters and ketones, such as ethyl acetate, acetone, and 2-butanone; polar aprotic solvents, such as acetonitrile, dimethylsulfoxide, dimethylformamide, pyridine, and the like; or combinations of two or more solvents. In a preferred embodiment, the solvent is a halogenated aliphatic hydrocarbon. In a more preferred embodiment, the solvent is chloroform, dichloromethane, or dichloroethane. In certain instances, the reaction may be conducted in the absence of solvent, i.e., neat.

The reaction can be conducted over a range of temperatures. In certain instances, the reaction is conducted at temperature in the range of about −30° C. to about 150° C. In certain instances, the reaction is conducted at temperature in the range of about 0° C. to about 90° C. In certain instances, the reaction is conducted at temperature in the range of about 10° C. to about 50° C. In a preferred embodiment, the reaction is conducted at temperature in the range of about 15° C. to about 30° C. In certain instances, the reaction is conducted in an inert atmosphere, e.g., nitrogen or argon. In certain instances, the reaction environment is anhydrous. In certain instances, the reaction mixture contains less than about 4% by weight water. In certain instances, the reaction mixture contains less than about 2% by weight water. In certain instances, the reaction mixture contains less than about 1% by weight water. In certain instances, the compound comprising a nucleophilic functional group is attached to a solid support. In certain instances, the solid support is polystyrene or controlled pore glass.

A large variety of nucleophilic functional groups are amenable to the present invention. Representative examples of nucleophilic functional groups amenable to the present invention include amine, hydroxyl, selenol, alkoxide, selenide, —N($R^{12}$)M, ketone, ester, amide, silylenolether, phosphine, malonate, β-ketoester, α-nitroester, α-cyanoester, α-phosphonoester, or α-ketophosphonate; wherein $R^{12}$ is alkyl, aryl, or aralkyl; and M is an alkali metal or transitional metal with an overall charge of +1. In a preferred embodiment, the nucleophilic functional group is an amine or hydroxyl. In a more preferred embodiment, the nucleophilic functional group is an amine.

DEFINITIONS

For convenience, certain terms employed in the specification, examples, and appended claims are collected here.

The subscript "f" as used herein refers to an alkyl, alkenyl, aryl, aralkyl, or acyl moiety as described below, wherein substantially all or all of the hydrogens have been replaced with fluorines. In certain embodiments, greater than about 80% of the hydrogens have been replaced with fluorines. In certain embodiments, greater than about 90% of the hydrogens have been replaced with fluorines. In certain embodiments, greater than about 95% of the hydrogens have been replaced with fluorines. In certain embodiments, about 100% of the hydrogens have been replaced with fluorines. In certain embodiments, the subscript "f" as applied to an alkyl moiety refers to an alkyl group represented by "—$CH_2(CF_2)_nCF_3$" or "—$(CF_2)_nCF_3$", wherein n is an integer in range 1 to 20.

The term "heteroatom" as used herein means an atom of any element other than carbon or hydrogen. Preferred heteroatoms are boron, nitrogen, oxygen, phosphorus, sulfur and selenium.

The term "nucleophilic functional group" is recognized in the art, and as used herein means a chemical moiety having a reactive pair of electrons. Examples of nucleophilic functional groups include uncharged compounds such as amines, thiol, and hydroxyl, and charged moieties such as alkoxides, thiolates, carbanions, and a variety of organic anions.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry*, McGraw Hill Book Company, New York, (1977 edition) pp. 251-259. The Hammett constant values are generally negative for electron donating groups (σ[P]=−0.66 for $NH_2$) and positive for electron withdrawing groups (σ[P]=0.78 for a nitro group), σ[P] indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

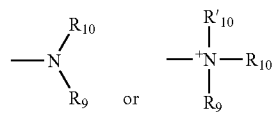

wherein $R_9$, $R_{10}$ and $R'_{10}$ each independently represent a group permitted by the rules of valence.

The term "acylamino" is art-recognized and refers to a moiety that can be represented by the general formula:

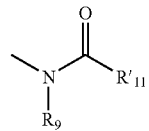

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

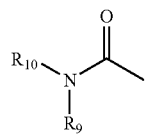

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

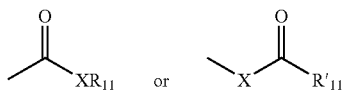

wherein X is a bond or represents an oxygen or a sulfur, and R$_{11}$ represents a hydrogen, an alkyl, an alkenyl, —S—(CH$_2$)$_m$—R$_8$ or a pharmaceutically acceptable salt, R'$_{11}$ represents a hydrogen, an alkyl, an alkenyl or —S—(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiolcarbonyl" group. Where X is a sulfur and R$_{11}$ or R'$_{11}$ is not hydrogen, the formula represents a "thiolester." Where X is a sulfur and R$_{11}$ is hydrogen, the formula represents a "thiolcarboxylic acid." Where X is a sulfur and R'$_{11}$ is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The term "sulfonate" is art recognized and includes a moiety that can be represented by the general formula:

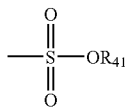

in which R$_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The term "sulfate" is art recognized and includes a moiety that can be represented by the general formula:

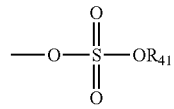

in which R$_{41}$ is as defined above.

The term "sulfonylamino" is art recognized and includes a moiety that can be represented by the general formula:

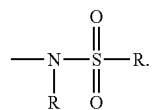

The term "sulfamoyl" is art-recognized and includes a moiety that can be represented by the general formula:

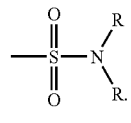

The term "sulfonyl", as used herein, refers to a moiety that can be represented by the general formula:

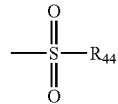

in which R$_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

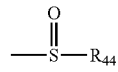

in which R$_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R$_7$, m and R$_7$ being defined above.

The term "selenol" refers to R—SeH, wherein R can be alkyl, heteralkyl, cycloalkyl, heterocycloalkyl, aryl, or aralkyl.

The term "selenide" refers to R—SeM, wherein R can be alkyl, heteralkyl, cycloalkyl, heterocycloalkyl, aryl, or aralkyl; and M is an alkali metal or transitional metal with an overall charge of +1.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "malonate" is art recognized and includes a moiety that can be represented by the general formula:

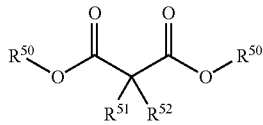

wherein $R^{50}$ represents independently for each occurrence alkyl, cycloalkyl, heterocycloalkyl, aryl, or aralkyl; $R^{51}$ is H, alkyl, cycloalkyl, heterocycloalkyl, aryl, or aralkyl; and $R^{52}$ is a radical, H, alkyl, cycloalkyl, heterocycloalkyl, aryl, or aralkyl.

The term "β-ketoester" is art recognized and includes a moiety that can be represented by the general formula:

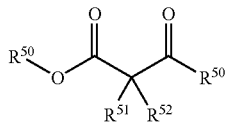

wherein $R^{50}$ represents independently for each occurrence alkyl, cycloalkyl, heterocycloalkyl, aryl, or aralkyl; $R^{51}$ is H, alkyl, cycloalkyl, heterocycloalkyl, aryl, or aralkyl; and $R^{52}$ is a radical, H, alkyl, cycloalkyl, heterocycloalkyl, aryl, or aralkyl.

The term "α-nitroester" is art recognized and includes a moiety that can be represented by the general formula:

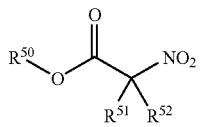

wherein $R^{50}$ is alkyl, cycloalkyl, heterocycloalkyl, aryl, or aralkyl; $R^{51}$ is H, alkyl, cycloalkyl, heterocycloalkyl, aryl, or aralkyl; and $R^{52}$ is a radical, H, alkyl, cycloalkyl, heterocycloalkyl, aryl, or aralkyl.

The term "α-cyanoester" is art recognized and includes a moiety that can be represented by the general formula:

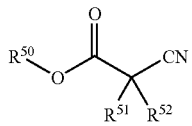

wherein $R^{50}$ is alkyl, cycloalkyl, heterocycloalkyl, aryl, or aralkyl; $R^{51}$ is H, alkyl, cycloalkyl, heterocycloalkyl, aryl, or aralkyl; and $R^{52}$ is a radical, H, alkyl, cycloalkyl, heterocycloalkyl, aryl, or aralkyl.

The term "α-phosphonoester" is art recognized and includes a moiety that can be represented by the general formula:

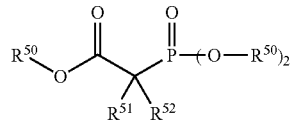

wherein $R^{50}$ represents independently for each occurrence alkyl, cycloalkyl, heterocycloalkyl, aryl, or aralkyl; $R^{51}$ is H, alkyl, cycloalkyl, heterocycloalkyl, aryl, or aralkyl; and $R^{52}$ is a radical, H, alkyl, cycloalkyl, heterocycloalkyl, aryl, or aralkyl.

The term "α-ketophosphonate" is art recognized and includes a moiety that can be represented by the general formula:

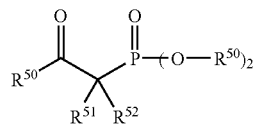

wherein $R^{50}$ represents independently for each occurrence alkyl, cycloalkyl, heterocycloalkyl, aryl, or aralkyl; $R^{51}$ is H, alkyl, cycloalkyl, heterocycloalkyl, aryl, or aralkyl; and $R^{52}$ is a radical, H, alkyl, cycloalkyl, heterocycloalkyl, aryl, or aralkyl.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

Compounds of the Invention

One aspect of the present invention relates to a compound represented by formula I:

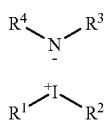

wherein $R^1$ is fluoroalkyl, fluoroheteroalkyl, fluorocycloalkyl, fluoroheterocycloalkyl, fluorocycloalkyl($C_1$-$C_6$)alkyl, fluoroheterocycloalkyl($C_1$-$C_6$)alkyl, (fluoroalkyl)aralkyl, fluoroaralkyl, or fluoroalkenyl($C_1$-$C_6$)alkyl;

$R^2$ is aryl, heteroaryl, alkenyl, or alkynyl;

$R^3$ and $R^4$ represent independently for each occurrence —$SO_2R^5$, —$C(O)R^5$, —$CO_2R^5$, —$C(O)N(R^6)_2$, —$C(S)R^5$, —$C(S)OR^5$, —$C(S)N(R^6)_2$, or -aryl-$(R^7)_n$;

$R^5$ represents independently for each occurrence alkyl, fluoroalkyl, chloroalkyl, alkenyl, aryl, or aralkyl;

$R^6$ represents independently for each occurrence H, alkyl, fluoroalkyl, chloroalkyl, aryl, or aralkyl;

$R^7$ represents independently for each occurrence nitro, cyano, halogen, —$SO_2R^5$, —$C(O)R^5$, —$CO_2R^5$, or —$C(O)N(R^6)_2$; and n is independently 0, 1, 2, 3, 4, or 5 in accord with the rules of valence.

In certain embodiments, the present invention relates to compound I, wherein $R^1$ is fluoroalkyl, fluoroheteroalkyl, fluorocycloalkyl($C_1$-$C_6$)alkyl, fluoroheterocycloalkyl($C_1$-$C_6$)alkyl, or fluoroaralkyl.

In certain embodiments, the present invention relates to compound I, wherein $R^1$ is fluoroalkyl or fluorocycloalkyl($C_1$-$C_6$)alkyl.

In certain embodiments, the present invention relates to compound I, wherein $R^1$ is fluoroalkyl.

In certain embodiments, the present invention relates to compound I, wherein $R^1$ is represented by formula:

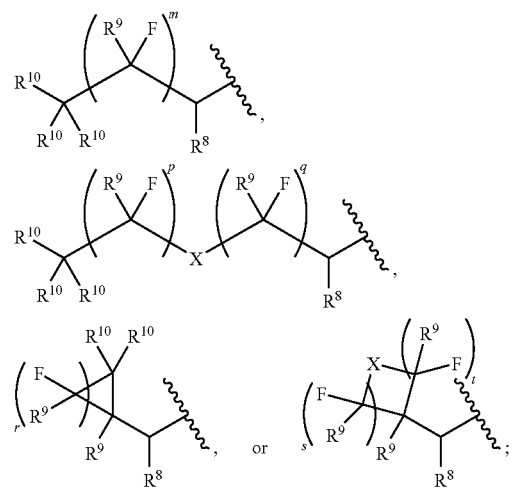

wherein $R^8$ is H, alkyl, or fluoroalkyl; $R^9$ is H, F, alkyl, or fluoroalkyl; $R^{10}$ is H or F; X is O, $NR^5$, or S; m is 1-18 inclusive; p is 0-10 inclusive; q is 1-10 inclusive; r is 1, 2, 3, 4, 5, 6, 7, or 8; s is 1, 2, 3, 4, 5, or 6; and t is 0, 1, 2, 3, 4, 5, or 6.

In certain embodiments, the present invention relates to compound I, wherein $R^1$ is represented by formula:

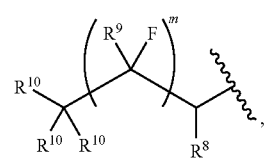

wherein $R^8$ is H, alkyl, or fluoroalkyl; $R^9$ is H, F, alkyl, or fluoroalkyl; $R^{10}$ is H or F; and m is 1-18 inclusive.

In certain embodiments, the present invention relates to compound I, wherein $R^1$ is represented by formula:

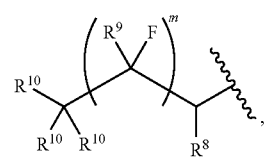

wherein $R^8$ is H; $R^9$ is H or F; $R^{10}$ is H or F; and m is 3-10 inclusive.

In certain embodiments, the present invention relates to compound I, wherein $R^1$ is —$CH_2(CF_2)_mCF_3$ and m is 3-10 inclusive.

In certain embodiments, the present invention relates to compound I, wherein $R^1$ is —$CH_2(CF_2)_4CF_3$.

In certain embodiments, the present invention relates to compound I, wherein $R^1$ is —$CH_2(CF_2)_6CF_3$.

In certain embodiments, the present invention relates to compound I, wherein $R^1$ is —$CH_2(CF_2)_8CF_3$.

In certain embodiments, the present invention relates to compound I, wherein $R^1$ is —$CH_2(CF_2)_{10}CF_3$.

In certain embodiments, the present invention relates to compound I, wherein $R^2$ is aryl.

In certain embodiments, the present invention relates to compound I, wherein $R^2$ is optionally substituted phenyl.

In certain embodiments, the present invention relates to compound I, wherein $R^2$ is phenyl.

In certain embodiments, the present invention relates to compound I, wherein $R^3$ and $R^4$ represent independently for each occurrence —$SO_2R^5$, —$C(O)R^5$, or —$CO_2R^5$.

In certain embodiments, the present invention relates to compound I, wherein $R^3$ and $R^4$ represent independently for each occurrence —$SO_2R^5$.

In certain embodiments, the present invention relates to compound I, wherein $R^3$ and $R^4$ represent independently for each occurrence —$SO_2R^5$, and $R^5$ is alkyl or fluoroalkyl.

In certain embodiments, the present invention relates to compound I, wherein $R^3$ and $R^4$ are —$SO_2CF_3$.

In certain embodiments, the present invention relates to compound I, wherein $R^1$ is —$CH_2(CF_2)_6CF_3$ and $R^2$ is phenyl.

In certain embodiments, the present invention relates to compound I, wherein $R^1$ is —$CH_2(CF_2)_8CF_3$ and $R^2$ is phenyl.

In certain embodiments, the present invention relates to compound I, wherein $R^1$ is —$CH_2(CF_2)_6CF_3$; $R^2$ is phenyl; and $R^3$ and $R^4$ are —$SO_2CF_3$.

In certain embodiments, the present invention relates to compound I, wherein $R^1$ is —$CH_2(CF_2)_8CF_3$; $R^2$ is phenyl; and $R^3$ and $R^4$ are —$SO_2CF_3$.

Methods of the Invention

One aspect of the present invention relates to a method of preparing a trivalent iodonium compound D comprising the step of combining A, B, and C; wherein is $R^1$—I—$(O_2CR^{11})_2$;   A is 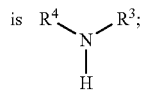   B is $R^2$—H;   C is 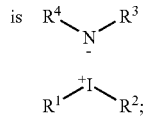   D $R^1$ is fluoroalkyl, fluoroheteroalkyl, fluorocycloalkyl, fluoroheterocycloalkyl, fluorocycloalkyl($C_1$-$C_6$)alkyl, fluoroheterocycloalkyl($C_1$-$C_6$)alkyl, (fluoroalkyl)aralkyl, fluoroaralkyl, or fluoroalkenyl($C_1$-$C_6$)alkyl;

$R^2$ is aryl, heteroaryl, alkenyl, or alkynyl;

$R^3$ and $R^4$ represent independently for each occurrence —$SO_2R^5$, —$C(O)R^5$, —$CO_2R^5$, —$C(O)N(R^6)_2$, —$C(S)R^5$, —$C(S)OR^5$, —$C(S)N(R^6)_2$, or -aryl-$(R^7)_n$;

$R^5$ represents independently for each occurrence alkyl, fluoroalkyl, chloroalkyl, aryl, or aralkyl;

$R^6$ represents independently for each occurrence H, alkyl, fluoroalkyl, chloroalkyl, aryl, or aralkyl;

$R^7$ represents independently for each occurrence nitro, cyano, halogen, —$SO_2R^5$, —$C(O)R^5$, —$CO_2R^5$, or —$C(O)N(R^6)_2$;

$R^{11}$ is alkyl, fluoroalkyl, aryl, or aralkyl; and n is independently 0, 1, 2, 3, 4, or 5 in accord with the rules of valence.

Another aspect of the present invention relates to a method of preparing a trivalent iodonium compound represented by Scheme 2:

Scheme 2

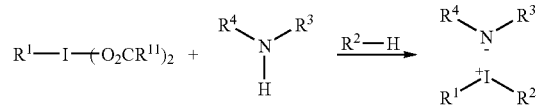

wherein $R^1$ is fluoroalkyl, fluoroheteroalkyl, fluorocycloalkyl, fluoroheterocycloalkyl, fluorocycloalkyl($C_1$-$C_6$)alkyl, fluoroheterocycloalkyl($C_1$-$C_6$)alkyl, (fluoroalkyl)aralkyl, fluoroaralkyl, or fluoroalkenyl($C_1$-$C_6$)alkyl;

$R^2$ is aryl, heteroaryl, alkenyl, or alkynyl;

$R^3$ and $R^4$ represent independently for each occurrence —$SO_2R^5$, —$C(O)R^5$, —$CO_2R^5$, —$C(O)N(R^6)_2$, —$C(S)R^5$, —$C(S)OR^5$, —$C(S)N(R^6)_2$, or -aryl-$(R^7)_n$;

$R^5$ represents independently for each occurrence alkyl, fluoroalkyl, chloroalkyl, aryl, or aralkyl;

$R^6$ represents independently for each occurrence H, alkyl, fluoroalkyl, chloroalkyl, aryl, or aralkyl;

$R^7$ represents independently for each occurrence nitro, cyano, halogen, —$SO_2R^5$, —$C(O)R^5$, —$CO_2R^5$, or —$C(O)N(R^6)_2$;

$R^{11}$ is alkyl, fluoroalkyl, aryl, or aralkyl; and n is independently 0, 1, 2, 3, 4, or 5 in accord with the rules of valence.

In certain embodiments, the present invention relates to the aforementioned method, wherein the reaction is performed in the presence of a perfluorohydrocarbon solvent.

In certain embodiments, the present invention relates to the aforementioned method, wherein the reaction is performed in the presence of a perfluorohexane.

In certain embodiments, the present invention relates to the aforementioned method, wherein the reaction is performed in the presence of an alkylacid anhydride, fluoroalkylacid anhydride, arylacid anhydride, or aralkylacid anhydride.

In certain embodiments, the present invention relates to the aforementioned method, wherein the reaction is performed in the presence of trifluoroacetic anhydride.

In certain embodiments, the present invention relates to the aforementioned method, wherein the reaction is performed in the presence of a perfluorohexane and trifluoroacetic anhydride.

In certain embodiments, the present invention relates to the aforementioned method, wherein is $R^1$ is fluoroalkyl, fluoroheteroalkyl, fluorocycloalkyl($C_1$-$C_6$)alkyl, fluoroheterocycloalkyl($C_1$-$C_6$)alkyl, or fluoroaralkyl.

In certain embodiments, the present invention relates to the aforementioned method, wherein $R^1$ is fluoroalkyl or fluorocycloalkyl($C_1$-$C_6$)alkyl.

In certain embodiments, the present invention relates to the aforementioned method, wherein $R^1$ is fluoroalkyl.

In certain embodiments, the present invention relates to the aforementioned method, wherein $R^1$ is represented by formula:

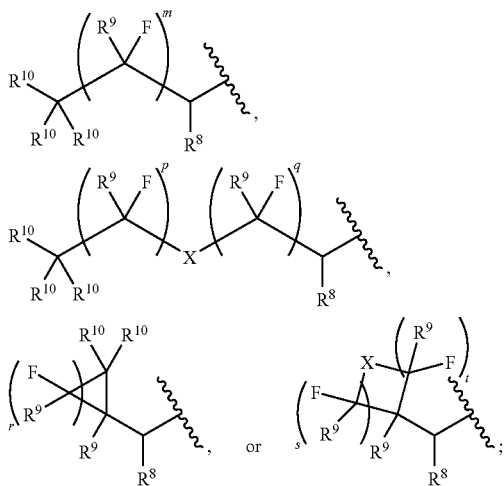

wherein $R^8$ is H, alkyl, or fluoroalkyl; $R^9$ is H, F, alkyl, or fluoroalkyl; $R^{10}$ is H or F; X is O, $NR^5$, or S; m is 1-18 inclusive; p is 0-10 inclusive; q is 1-10 inclusive; r is 1, 2, 3, 4, 5, 6, 7, or 8; s is 1, 2, 3, 4, 5, or 6; and t is 0, 1, 2, 3, 4, 5, or 6.

In certain embodiments, the present invention relates to the aforementioned method, wherein $R^1$ is represented by formula:

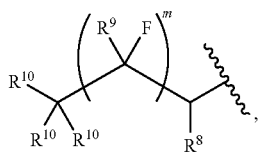

wherein $R^8$ is H, alkyl, or fluoroalkyl; $R^9$ is H, F, alkyl, or fluoroalkyl; $R^{10}$ is H or F; and m is 1-18 inclusive.

In certain embodiments, the present invention relates to the aforementioned method, wherein $R^1$ is represented by formula:

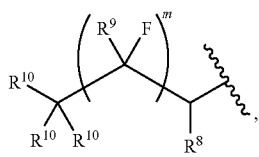

wherein $R^8$ is H; $R^9$ is H or F; $R^{10}$ is H or F; and m is 3-10 inclusive.

In certain embodiments, the present invention relates to the aforementioned method, wherein $R^1$ is —$CH_2(CF_2)_mCF_3$ and m is 3-10 inclusive.

In certain embodiments, the present invention relates to the aforementioned method, wherein $R^1$ is —$CH_2(CF_2)_4CF_3$.

In certain embodiments, the present invention relates to the aforementioned method, wherein $R^1$ is —$CH_2(CF_2)_6CF_3$.

In certain embodiments, the present invention relates to the aforementioned method, wherein $R^1$ is —$CH_2(CF_2)_8CF_3$.

In certain embodiments, the present invention relates to the aforementioned method, wherein $R^1$ is —$CH_2(CF_2)_{10}CF_3$.

In certain embodiments, the present invention relates to the aforementioned method, wherein $R^2$ is aryl.

In certain embodiments, the present invention relates to the aforementioned method, wherein $R^2$ is optionally substituted phenyl.

In certain embodiments, the present invention relates to the aforementioned method, wherein $R^2$ is phenyl.

In certain embodiments, the present invention relates to the aforementioned method, wherein $R^3$ and $R^4$ represent independently for each occurrence —$SO_2R^5$, —$C(O)R^5$, or —$CO_2R^5$.

In certain embodiments, the present invention relates to the aforementioned method, wherein $R^3$ and $R^4$ represent independently for each occurrence —$SO_2R^5$.

In certain embodiments, the present invention relates to the aforementioned method, wherein $R^3$ and $R^4$ represent independently for each occurrence —$SO_2R^5$, and $R^5$ is alkyl or fluoroalkyl.

In certain embodiments, the present invention relates to the aforementioned method, wherein $R^3$ and $R^4$ are —$SO_2CF_3$.

In certain embodiments, the present invention relates to the aforementioned method, wherein $R^1$ is —$CH_2(CF_2)_6CF_3$ and $R^2$ is phenyl.

In certain embodiments, the present invention relates to the aforementioned method, wherein $R^1$ is —$CH_2(CF_2)_8CF_3$ and $R^2$ is phenyl.

In certain embodiments, the present invention relates to the aforementioned method, wherein $R^1$ is —$CH_2(CF_2)_6CF_3$; $R^2$ is phenyl; and $R^3$ and $R^4$ are —$SO_2CF_3$.

In certain embodiments, the present invention relates to the aforementioned method, wherein $R^1$ is —$CH_2(CF_2)_8CF_3$; $R^2$ is phenyl; and $R^3$ and $R^4$ are —$SO_2CF_3$.

Another aspect of the present invention relates to a method of preparing a fluorocarbon compound, comprising the step of:

treating a compound comprising a nucleophilic functional group with a trivalent iodonium compound to generate a fluorocarbon compound, wherein said trivalent iodonium compound is represented by formula I:

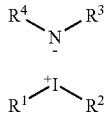

I wherein $R^1$ is fluoroalkyl, fluoroheteroalkyl, fluorocycloalkyl, fluoroheterocycloalkyl, fluorocycloalkyl($C_1$-$C_6$)alkyl, fluoroheterocycloalkyl($C_1$-$C_6$)alkyl, (fluoroalkyl)aralkyl, fluoroaralkyl, or fluoroalkenyl($C_1$-$C_6$)alkyl;

$R^2$ is aryl, heteroaryl, alkenyl, or alkynyl;

$R^3$ and $R^4$ represent independently for each occurrence —$SO_2R^5$, —$C(O)R^5$, —$CO_2R^5$, —$C(O)N(R^6)_2$, —$C(S)R^5$, —$C(S)OR^5$, —$C(S)N(R^6)_2$, or -aryl-$(R^7)_n$;

$R^5$ represents independently for each occurrence alkyl, fluoroalkyl, chloroalkyl, aryl, or aralkyl;

$R^6$ represents independently for each occurrence H, alkyl, fluoroalkyl, chloroalkyl, aryl, or aralkyl;

$R^7$ represents independently for each occurrence nitro, cyano, halogen, $SO_2R^5$, —$C(O)R^5$, —$CO_2R^5$, or —$C(O)N(R^6)_2$;

$R^{11}$ is alkyl, fluoroalkyl, aryl, or aralkyl; and n is independently 0, 1, 2, 3, 4, or 5 in accord with the rules of valence.

In certain embodiments, the present invention relates to the aforementioned method, wherein the reaction is performed in the presence of a non-nucleophilic base.

In certain embodiments, the present invention relates to the aforementioned method, wherein the reaction is performed in the presence of pyridine, 2,4-dimethylpyridine, collidine, pyridine, 2,6-di-tetrabutylpyridine, 1,8-diazabicyclo[4.3.0]non-5-ene, triethylamine, diisopropylethylamine, or dicyclohexylamine.

In certain embodiments, the present invention relates to the aforementioned method, wherein the reaction is performed in the presence of collidine.

In certain embodiments, the present invention relates to the aforementioned method, wherein said compound comprising a nucleophilic functional group is a peptide, oligosaccharide, oligonucleotide, or small organic compound.

In certain embodiments, the present invention relates to the aforementioned method, wherein said compound comprising a nucleophilic functional group is a peptide.

In certain embodiments, the present invention relates to the aforementioned method, wherein said compound comprising a nucleophilic functional group is a peptide having between 2 and about 100 amino acid residues.

In certain embodiments, the present invention relates to the aforementioned method, wherein said compound comprising a nucleophilic functional group is a peptide having between 2 and about 50 amino acid residues.

In certain embodiments, the present invention relates to the aforementioned method, wherein said compound comprising a nucleophilic functional group is a peptide having between 2 and about 25 amino acid residues.

In certain embodiments, the present invention relates to the aforementioned method, wherein said compound comprising a nucleophilic functional group is a oligosaccharide.

In certain embodiments, the present invention relates to the aforementioned method, wherein said compound comprising a nucleophilic functional group is a oligosaccharide having about 2-20 sugar residues.

In certain embodiments, the present invention relates to the aforementioned method, wherein said compound comprising a nucleophilic functional group is a oligosaccharide having about 2-10 sugar residues.

In certain embodiments, the present invention relates to the aforementioned method, wherein said compound comprising a nucleophilic functional group is a small organic compound with a molecular weight less than about 900 g/mol.

In certain embodiments, the present invention relates to the aforementioned method, wherein said small organic compound is represented by formula II:

$$A^1 - X^1 \quad\quad II$$

wherein $A^1$ is optionally substituted alkyl, optionally substituted heteroalkyl, optionally substituted cycloalkyl, optionally substituted heterocycloalkyl, aryl, or aralkyl; and $X^1$ is —NH$_2$, —NHalkyl, —NHaralkyl, —OH, —SH, or —SeH.

In certain embodiments, the present invention relates to the aforementioned method, wherein said compound comprising a nucleophilic functional group is bound to a solid support.

In certain embodiments, the present invention relates to the aforementioned method, wherein said nucleophilic functional group is an amine, hydroxyl, selenol, alkoxide, selenide, —N($R^{12}$)M, ketone, ester, amide, silylenolether, phosphine, malonate, β-ketoester, α-nitroester, α-cyanoester, α-phosphonoester, or α-ketophosphonate; wherein $R^{12}$ is alkyl, aryl, or aralkyl; and M is an alkali metal or transitional metal with an overall charge of +1.

In certain embodiments, the present invention relates to the aforementioned method, wherein said nucleophilic functional group is an amine or hydroxyl.

In certain embodiments, the present invention relates to the aforementioned method, wherein said nucleophilic functional group is an amine.

In certain embodiments, the present invention relates to the aforementioned method, wherein is $R^1$ is fluoroalkyl, fluoroheteroalkyl, fluorocycloalkyl($C_1$-$C_6$)alkyl, fluoroheterocycloalkyl($C_1$-$C_6$)alkyl, or fluoroaralkyl.

In certain embodiments, the present invention relates to the aforementioned method, wherein $R^1$ is fluoroalkyl or fluorocycloalkyl($C_1$-$C_6$)alkyl.

In certain embodiments, the present invention relates to the aforementioned method, wherein $R^1$ is fluoroalkyl.

In certain embodiments, the present invention relates to the aforementioned method, wherein $R^1$ is represented by formula:

wherein $R^8$ is H, alkyl, or fluoroalkyl; $R^9$ is H, F, alkyl, or fluoroalkyl; $R^{10}$ is H or F; X is O, NR$^5$, or S; m is 1-18 inclusive; p is 0-10 inclusive; q is 1-10 inclusive; r is 1, 2, 3, 4, 5, 6, 7, or 8; s is 1, 2, 3, 4, 5, or 6; and t is 0, 1, 2, 3, 4, 5, or 6.

In certain embodiments, the present invention relates to the aforementioned method, wherein $R^1$ is represented by formula:

wherein $R^8$ is H, alkyl, or fluoroalkyl; $R^9$ is H, F, alkyl, or fluoroalkyl; $R^{10}$ is H or F; and m is 1-18 inclusive.

In certain embodiments, the present invention relates to the aforementioned method, wherein $R^1$ is represented by formula:

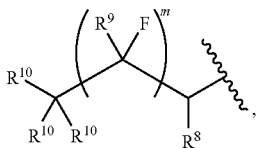

wherein $R^8$ is H; $R^9$ is H or F; $R^{10}$ is H or F; and m is 3-10 inclusive.

In certain embodiments, the present invention relates to the aforementioned method, wherein $R^1$ is —$CH_2(CF_2)_mCF_3$ and m is 3-10 inclusive.

In certain embodiments, the present invention relates to the aforementioned method, wherein $R^1$ is —$CH_2(CF_2)_4CF_3$.

In certain embodiments, the present invention relates to the aforementioned method, wherein $R^1$ is —$CH_2(CF_2)_6CF_3$.

In certain embodiments, the present invention relates to the aforementioned method, wherein $R^1$ is —$CH_2(CF_2)_8CF_3$.

In certain embodiments, the present invention relates to the aforementioned method, wherein $R^1$ is —$CH_2(CF_2)_{10}CF_3$.

In certain embodiments, the present invention relates to the aforementioned method, wherein $R^2$ is aryl.

In certain embodiments, the present invention relates to the aforementioned method, wherein $R^2$ is optionally substituted phenyl.

In certain embodiments, the present invention relates to the aforementioned method, wherein $R^2$ is phenyl.

In certain embodiments, the present invention relates to the aforementioned method, wherein $R^3$ and $R^4$ represent independently for each occurrence —$SO_2R^5$, —$C(O)R^5$, or —$CO_2R^5$.

In certain embodiments, the present invention relates to the aforementioned method, wherein $R^3$ and $R^4$ represent independently for each occurrence —$SO_2R^5$.

In certain embodiments, the present invention relates to the aforementioned method, wherein $R^3$ and $R^4$ represent independently for each occurrence —$SO_2R^5$, and $R^5$ is alkyl or fluoroalkyl.

In certain embodiments, the present invention relates to the aforementioned method, wherein $R^3$ and $R^4$ are —$SO_2CF_3$.

In certain embodiments, the present invention relates to the aforementioned method, wherein $R^1$ is —$CH_2(CF_2)_6CF_3$ and $R^2$ is phenyl.

In certain embodiments, the present invention relates to the aforementioned method, wherein $R^1$ is —$CH_2(CF_2)_8CF_3$ and $R^2$ is phenyl.

In certain embodiments, the present invention relates to the aforementioned method, wherein $R^1$ is —$CH_2(CF_2)_6CF_3$; $R^2$ is phenyl; and $R^3$ and $R^4$ are —$SO_2CF_3$.

In certain embodiments, the present invention relates to the aforementioned method, wherein $R^1$ is —$CH_2(CF_2)_8CF_3$; $R^2$ is phenyl; and $R^3$ and $R^4$ are —$SO_2CF_3$.

Another aspect of the present invention relates to a method of purifying a compound, comprising the steps of:

treating a mixture comprising a first compound and a second compound with a trivalent iodonium compound to generate a mixture of said first compound and a fluorocarbon compound leaving said first compound unchanged, and purifying said mixture by fluorous liquid-liquid extraction, fluorous solid-phase extraction, fluorous chromatography, or centrifugation; wherein said first compound and said second compound each represent independently a peptide, oligosaccharide, oligonucleotide, or small organic compound; and said trivalent iodonium compound is represented by formula I:

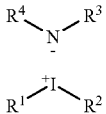

wherein $R^1$ is fluoroalkyl, fluoroheteroalkyl, fluorocycloalkyl, fluoroheterocycloalkyl, fluorocycloalkyl($C_1$-$C_6$)alkyl, fluoroheterocycloalkyl($C_1$-$C_6$)alkyl, (fluoroalkyl)aralkyl, fluoroaralkyl, or fluoroalkenyl($C_1$-$C_6$)alkyl;

$R^2$ is aryl, heteroaryl, alkenyl, or alkynyl;

$R^3$ and $R^4$ represent independently for each occurrence —$SO_2R^5$, —$C(O)R^5$, —$CO_2R^5$, —$C(O)N(R^6)_2$, —$C(S)R^5$, —$C(S)OR^5$, —$C(S)N(R^6)_2$, or aryl-$(R^7)_n$;

$R^5$ represents independently for each occurrence alkyl, fluoroalkyl, chloroalkyl, aryl, or aralkyl;

$R^6$ represents independently for each occurrence H, alkyl, fluoroalkyl, chloroalkyl, aryl, or aralkyl;

$R^7$ represents independently for each occurrence nitro, cyano, halogen, —$SO_2R^5$, —$C(O)R^5$, —$CO_2R^5$, or —$C(O)N(R^6)_2$; and n is independently 0, 1, 2, 3, 4, or 5 in accord with the rules of valence.

In certain embodiments, the present invention relates to the aforementioned method, wherein said mixture is purified by fluorous chromatography.

In certain embodiments, the present invention relates to the aforementioned method, wherein said mixture is purified by flash column chromatography using fluorous silica gel or high performance liquid chromatography using a fluorous silica gel column.

In certain embodiments, the present invention relates to the aforementioned method, wherein said first compound and said second compound each represent independently a peptide.

In certain embodiments, the present invention relates to the aforementioned method, wherein said first compound and said second compound each represent independently a peptide having between 2 and about 100 amino acid residues.

In certain embodiments, the present invention relates to the aforementioned method, wherein said first compound and said second compound each represent independently a peptide having between 2 and about 50 amino acid residues.

In certain embodiments, the present invention relates to the aforementioned method, wherein said first compound and said second compound each represent independently a peptide having between 2 and about 25 amino acid residues.

In certain embodiments, the present invention relates to the aforementioned method, wherein said first compound and said second compound each represent independently a oligosaccharide.

In certain embodiments, the present invention relates to the aforementioned method, wherein said first compound and said second compound each represent independently a oligosaccharide having about 2-20 sugar residues.

In certain embodiments, the present invention relates to the aforementioned method, wherein said first compound and said second compound each represent independently a oligosaccharide having about 2-10 sugar residues.

In certain embodiments, the present invention relates to the aforementioned method, wherein said first compound and said second compound each represent independently a small organic compound with a molecular weight less than about 900 g/mol.

In certain embodiments, the present invention relates to the aforementioned method, wherein said compound is represented by formula II:

$$A^1-X^1 \quad \text{II}$$

wherein $A^1$ is alkyl, heteroalkyl, cycloalkyl, heterocycloalkyl, aryl, or aralkyl; and $X^1$ is —$NH_2$, NHalkyl, —NHaralkyl, —OH, —SH, or —SeH.

In certain embodiments, the present invention relates to the aforementioned method, wherein $R^1$ is fluoroalkyl, fluoroheteroalkyl, fluorocycloalkyl($C_1$-$C_6$)alkyl, fluoroheterocycloalkyl($C_1$-$C_6$)alkyl, or fluoroaralkyl.

In certain embodiments, the present invention relates to the aforementioned method, wherein $R^1$ is fluoroalkyl or fluorocycloalkyl($C_1$-$C_6$)alkyl.

In certain embodiments, the present invention relates to the aforementioned method, wherein $R^1$ is fluoroalkyl.

In certain embodiments, the present invention relates to the aforementioned method, wherein $R^1$ is represented by formula:

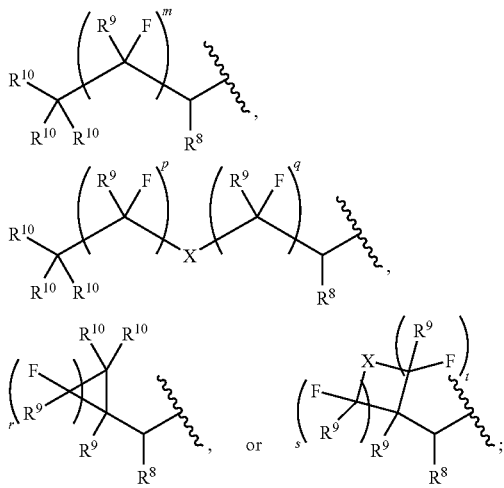

wherein $R^8$ is H, alkyl, or fluoroalkyl; $R^9$ is H, F, alkyl, or fluoroalkyl; $R^{10}$ is H or F; X is O, $NR^5$, or S; m is 1-18 inclusive; p is 0-10 inclusive; q is 1-10 inclusive; r is 1, 2, 3, 4, 5, 6, 7, or 8; s is 1, 2, 3, 4, 5, or 6; and t is 0, 1, 2, 3, 4, 5, or 6.

In certain embodiments, the present invention relates to the aforementioned method, wherein $R^1$ is represented by formula:

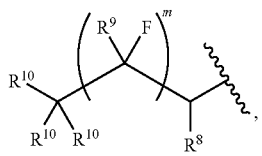

wherein $R^8$ is H, alkyl, or fluoroalkyl; $R^9$ is H, F, alkyl, or fluoroalkyl; $R^{10}$ is H or F; and m is 1-18 inclusive.

In certain embodiments, the present invention relates to the aforementioned method, wherein $R^1$ is represented by formula:

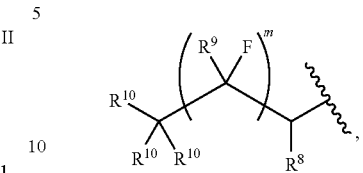

wherein $R^8$ is H; $R^9$ is H or F; $R^{10}$ is H or F; and m is 3-10 inclusive.

In certain embodiments, the present invention relates to the aforementioned method, wherein $R^1$ is —$CH_2(CF_2)_mCF_3$ and m is 3-10 inclusive.

In certain embodiments, the present invention relates to the aforementioned method, wherein $R^1$ is —$CH_2(CF_2)_4CF_3$.

In certain embodiments, the present invention relates to the aforementioned method, wherein $R^1$ is —$CH_2(CF_2)_6CF_3$.

In certain embodiments, the present invention relates to the aforementioned method, wherein $R^1$ is —$CH_2(CF_2)_8CF_3$.

In certain embodiments, the present invention relates to the aforementioned method, wherein $R^1$ is —$CH_2(CF_2)_{10}CF_3$.

In certain embodiments, the present invention relates to the aforementioned method, wherein $R^2$ is aryl.

In certain embodiments, the present invention relates to the aforementioned method, wherein $R^2$ is optionally substituted phenyl.

In certain embodiments, the present invention relates to the aforementioned method, wherein $R^2$ is phenyl.

In certain embodiments, the present invention relates to the aforementioned method, wherein $R^3$ and $R^4$ represent independently for each occurrence —$SO_2R^5$, —$C(O)R^5$, or —$CO_2R^5$.

In certain embodiments, the present invention relates to the aforementioned method, wherein $R^3$ and $R^4$ represent independently for each occurrence —$SO_2R^5$.

In certain embodiments, the present invention relates to the aforementioned method, wherein $R^3$ and $R^4$ represent independently for each occurrence —$SO_2R^5$, and $R^5$ is alkyl or fluoroalkyl.

In certain embodiments, the present invention relates to the aforementioned method, wherein $R^3$ and $R^4$ are —$SO_2CF_3$.

In certain embodiments, the present invention relates to the aforementioned method, wherein $R^1$ is —$CH_2(CF_2)_6CF_3$ and $R^2$ is phenyl.

In certain embodiments, the present invention relates to the aforementioned method, wherein $R^1$ is —$CH_2(CF_2)_8CF_3$ and $R^2$ is phenyl.

In certain embodiments, the present invention relates to the aforementioned method, wherein $R^1$ is —$CH_2(CF_2)_6CF_3$; $R^2$ is phenyl; and $R^3$ and $R^4$ are —$SO_2CF_3$.

In certain embodiments, the present invention relates to the aforementioned method, wherein $R^1$ is —$CH_2(CF_2)_8CF_3$; $R^2$ is phenyl; and $R^3$ and $R^4$ are —$SO_2CF_3$.

Combinatorial Libraries

The subject compounds may be synthesized using the methods of combinatorial synthesis described in this section. Combinatorial libraries of the compounds may be used for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116: 2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

[A] Direct Characterization: A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

[B] Multipin Synthesis: The libraries of the subject method can take the multipin library format. Briefly, Geysen and co-workers (Geysen et al. (1984) *PNAS* 81:3998-4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811-5814; Valerio et al. (1991) *Anal Biochem* 197:168-177; Bray et al. (1991) *Tetrahedron Lett* 32:6163-6166).

[C] Divide-Couple-Recombine: In yet another embodiment, a variegated library of compounds can be provided on a set of beads utilizing the strategy of divide-couple-recombine (see, e.g., Houghten (1985) *PNAS* 82:5131-5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

[D] Combinatorial Libraries by Light-Directed, Spatially Addressable Parallel Chemical Synthesis: A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271-280; Fodor, S. P. A. (1991) *Science* 251:767; Pirrung et al. (1992) U.S. Pat. No. 5,143,854; Jacobs et al. (1994) *Trends Biotechnol* 12:19-26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

[E] Encoded Combinatorial Libraries: In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

[E1] Tagging with sequenceable bio-oligomers: The principle of using oligonucleotides to encode combinatorial synthetic libraries was described in 1992 (Brenner et al. (1992) PNAS 89:5381-5383), and an example of such a library appeared the following year (Needles et al. (1993) *PNAS* 90:10700-10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529-2531), orthogonality in synthesis is achieved by employing acid-labile protection for the coding strand and base-labile protection for the compound strand.

In an alternative approach (Nikolaiev et al. (1993) *Pept Res* 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

[E2] Non-sequenceable Tagging: Binary Encoding: An alternative form of encoding the test compound library employs a set of non-sequencable electrophoric tagging molecules that are used as a binary code (Ohlmeyer et al. (1993) *PNAS* 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723-4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

Example 1

Peptide Synthesis

P1, P2, & P3

Peptides were prepared using the N-tert-butyloxycarbonyl (t-Boc) amino acid derivatives for Merrifield solid-phase synthesis (MBHA resin) using the in-situ neutralization protocol. See Schnolzer, M.; Alewood, P.; Jones, A.; Alewood.; D, Kent, S. B. *Int. J. Pept. Protein Res.* 1992, 40, 180-193. N-α-Boc-α-S-amino acids were used with standard side chain protecting groups.

At the points of intentional incomplete couplings, 0.8-0.9 equivalents of Boc-amino acid (0.12-0.135 mmol for a 0.15 mmol scale synthesis), 0.72-0.81 eq. HBTU, and 3.5 eq. DIEA were used.

Peptides were cleaved from the resin using high HF conditions (90% anhydrous HF/10% anisole at 0° C. for 2 hours). The crude reaction mixture after the cleavage reaction was washed with cold $Et_2O$. Peptides were extracted with 5×15 mL 10% AcOH, followed by 5×15 mL 50% $CH_3CN$ in water (containing 0.1% $CF_3COOH$).

The AcOH and $CH_3CN$ extracts were separately reduced to small volume using a rotary evaporator, the residues taken up in water and lyophilized.

Example 2

Preparation and Characterization of Reagent 1a

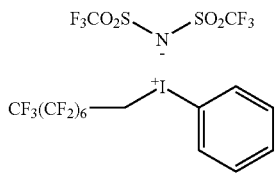

1a (Bis-trifluoroacetoxy)iodo-1H,1H-perfluorooctane (6.0 g, 8.2 mmol) was added in one portion to $(CF_3SO_2)_2NH$ (3.01 g, 10.7 mmol). The triflimide $(CF_3SO_2)_2NH$ should be blanketed with nitrogen because it strongly fumes and deliquesces in the air. The two solids were slurried in a mixture of FC-72 (perfluorohexane, 12 mL) and trifluoroacetic anhydride (3 mL). A clear solution formed within 15 minutes, at which point benzene (1.2 mL, 13.3 mmol) was added rapidly and the reaction mixture was stirred under nitrogen for 22 hrs at rt. Evaporation of the volatiles and stirring with ice/water produced a white precipitate. This was collected on a glass frit, dried, and further evacuated under vacuum yielding 6.12 g (85%) of 1a as a white powder, which was used directly in capping reactions. $^1H$ NMR ($CD_2Cl_2$, 300 MHz, ref. $CHDCl=5.3$ ppm) 4.8 (t, 2H, J=18 Hz, $CH_2R_f$), 7.6 (m, 2H), 7.8 (m, 1H), 8.2 (m, 2H). $^{19}F$ NMR ($CD_2Cl_2$, 282 MHz, ref. $C_6F_6=-162$ ppm) −80.6 (s, 6F, $SO_2CF_3$), −82.0 (m, 3F, $CF_3$), −105.0 (m, $CH_2CF_2$), −122.1 (4F, br s, two overlapping $CF_2$), −122.8 (2F, br s), −123.5 (2F, br s), −127.0 (2F, br s). For reference to (Bis-trifluoroacetoxy)iodo-1H,1H-perfluorooctane, see Umemoto, T.; Gotoh, Y. *J. Fluor. Chem.* 1985, 28, 235-239.

Example 3

Fluorous Capping with Reagent 1a

After the intentional deletion, the resin was washed with DMF (30 sec flow wash and 5×10 mL shake wash). The same wash sequence was repeated using $CH_2Cl_2$. Then 2 eq of a solution of 1a in $CH_2Cl_2$ (0.3 mmol, 260 mg in 5 mL $CH_2Cl_2$ for a 0.15 mmol scale synthesis) were added and the resin was mildly shaken for 1 min. Then a solution of 2 eq (40 μL for a 0.15 mmol scale synthesis) of 2,4,6-collidine in $CH_2Cl_2$ was added and mild shaking continued for 15 min. The resin was washed with $CH_2Cl_2$ and the capping step was repeated. Deprotection was performed with neat TFA after washing with $CH_2Cl_2$ (30 sec flow). After deprotection the resin was again swollen in DMF and the synthesis continued as usual.

Example 4

Mass Spectrometry (ESI-MS) of P1, P2, & P3

ESI-MS Conditions: Finnigan LTQ, Thermo Electron Corp.; solutions were ~100 nM in iPrOH/1% AcOH unless otherwise noted, flow rate: 5 mL/min, spray voltage: 5 kV, capillary voltage: 40 V. Sample identities: (1) crude obtained from cleavage reaction by resin extraction with 10% AcOH; (2) crude obtained from cleavage reaction by resin extraction with 1:1 $CH_3CN:H_2O$ (10% AcOH); (3) peak collected from Reverse Phase HPLC; and (4) pellet obtained by centrifugation of sample from (1) and redissolution in $MeOH/H_2O$ or $iPrOH/H_2O$. An (x) indicates not observed; Ac indicates capped with $Ac_2O$; and $R_f$ indicates $-CH_2(CF_2)_6CF_3$; and an asterisk indicates positions where the peptide coupling was incomplete.

TABLE 1

| Peptide P1 (Ac—NH—VEA*AID*YI*DA-CONH$_2$) | | | |
|---|---|---|---|
| Fragment | MW$_{calc}$ (Da) | MW$_{obsd}$ (Da) | Sample |
| Ac—NH—VEAAIDYIDA-CONH$_2$ | 1119.55 | 1142.55 (+Na) | 1 |
| Ac—NH-AIDYIDA-CONH$_2$ | 820.40 | 843.45 (+Na) | 1 |
| Ac—NH—YIDA-CONH$_2$ | 521.25 | x | x |
| Ac—NH—DA-CONH$_2$ | 245.10 | 268.18 (+Na) | 1 |
| Ac—NH—VEAAIDYIDA-CONH$_2$ | 1119.55 | 1120.36; 1142.55 (+Na) | 2 |
| R$_f$CH$_2$—NH-AIDYIDA-CONH$_2$ | 1160.37 | x | 2, 4 |
| R$_f$CH$_2$—NH—YIDA-CONH$_2$ | 861.22 | 862.18 | 2, 4 |
| R$_f$CH$_2$—NH—DA-CONH$_2$ | 585.07 | 586.09; 608.18 (+Na) | 2, 4 |

TABLE 2

Peptide P2
(Ac—NH-RAV*KVY*ADAA*EDESAEAFALEF—CONH$_2$)

| Fragment | MW$_{calc}$ (Da) | MW$_{obsd}$ (Da) | Sample |
|---|---|---|---|
| Ac—NH-RAVKVYADAAEDESAEAFALEF—CONH$_2$ | 2442.17 | 1222.64 | 1, 3 |
| Ac—NH—KVYADAAEDESAEAFALEF—CONH$_2$ | 2115.96 | 1070.55 (+Na) | 3 |
| Ac—NH-ADAAEDESAEAFALEF—CONH$_2$ | 1725.74 | 1748.82 (+Na) | 3 |
| Ac—NH-EDESAEAFALEF—CONH$_2$ | 1397.60 | 1420.73 (+Na) | 3 |
| Ac—NH-RAVKVYADAAEDESAEAFALEF—CONH$_2$ | 2442.17 | 1222.64 | 1, 2, 3 |
| R$_f$CH$_2$—NH—KVYADAAEDESAEAFALEF—CONH$_2$ | 2455.94 | x | 2 |
| R$_f$CH$_2$—NH-ADAAEDESAEAFALEF—CONH$_2$ | 2065.71 | 1020.55 (−H$_2$O +Na); 1056.00 (+2 Na) | 2 |
| R$_f$CH$_2$—NH-EDESAEAFALEF—CONH$_2$ | 1737.57 | 1760.54 (+Na); 1742.53 (−H$_2$O +Na) | 2 |

TABLE 3

Peptide P3 (Ac—NH—PT*GYGS*SSRRAPET-CONH$_2$)

| Fragment | MW$_{calc}$ (Da) | MW$_{obsd}$ (Da) | Sample |
|---|---|---|---|
| Ac—NH—PTGYGSSSRRAPET-CONH$_2$ | 1505.72 | 1506.73 | 1 |
| Ac—NH-GYGSSSRRAPET-CONH$_2$ | 1307.62 | 1308.64 | 1 |
| Ac—NH—SSRRAPET-CONH$_2$ | 943.48 | 969.6 (+Na); 923.9 (−H$_2$O) | 1 |
| Ac—NH—PTGYGSSSRRAPET-CONH$_2$ | 1505.72 | 1506.82 | 1, 3 |
| R$_f$CH$_2$—NH-GYGSSSRRAPET-CONH$_2$ | 1647.59 | 1648.64 | 1 |
| R$_f$CH$_2$—NH—SSRRAPET-CONH$_2$ | 1283.45 | 1284.45 | 1, 3 |

Example 4

Fluoroalkylation of Compound 2 with 1a

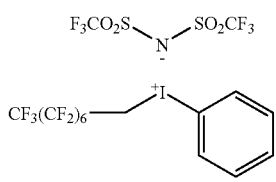

1a

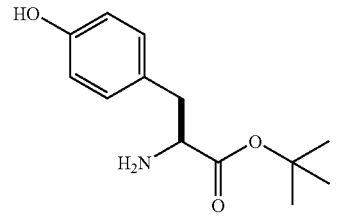

2

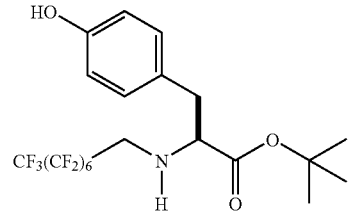

3c

Compound 2 (Tyr-OBut, 119 mg, 0.5 mmol), iodonium salt 1a (430 mg, 0.5 mmol), and 2,4,6-collidine (66 µL, 0.5 mmol) were stirred in CH$_2$Cl$_2$ (5 mL) at room temperature for 1 hour (by TLC the reaction was judged complete in 10 min). Evaporation to small volume and chromatography (Et$_2$O/hexanes 1/1) gave 248 mg (80%) of C$_7$F$_{15}$CH$_2$TyrOBut 3c as a white powder. $^1$H NMR (CDCl$_3$, 300 MHz, ref. TMS=0 ppm) 1.4 (s, 9H, But), 2.8-2.9 (m, 2H, tyrosine CH$_2$), 3.0-3.5 (ABX$_2$ m, 2H, R$_f$CF$_2$CH$_2$), 3.5 (t, 1H), 6.7 (d, 2H), 7.0 (d, 2H). $^{19}$F NMR (CDCl$_3$, 282 MHz, ref. C$_6$F$_6$=−162 ppm) −81.0 (m, 3F, CF$_3$), −118.4 (m, CH$_2$CF$_2$), −122.0 (4F, br s, two overlapping CF$_2$), −123.0 (2F, br s), −123.5 (2F, br s), −126.2 (2F, br s).

TyrOBut 2 (24 mg, 0.1 mmol), iodonium salt 1a (173 mg, 0.2 mmol), and 2,4,6-collidine (27 µL, 0.2 mmol) were stirred in CH$_2$Cl$_2$ (3 mL) at room temperature for 15 minutes (a typical capping reaction time), then DIEA (50 µL) was added to destroy any remaining iodonium salt. TLC and NMR analysis indicated no other product besides C$_7$F$_{15}$CH$_2$TyrOBut 3e.

Similarly, C$_7$F$_{15}$CH$_2$—NH-Tyr-OBut 3c (35 mg, 0.057 mmol), iodonium salt 1a (100 mg, 0.115 mmol) and 2,4,6-collidine (16 µL, 0.12 mmol) were stirred in CH$_2$Cl$_2$ (2 mL) at room temperature for 30 minutes. TLC indicated only C$_7$F$_{15}$CH$_2$—NH-Tyr-OBut 3c and PhI coproduct as the low polarity components. The reaction was quenched with DIEA (50 µL) and evaporated. Chromatography on silica gel (ether/hexanes 1/1) gave pure C$_7$F$_{15}$CH$_2$TyrOBut 3c (29 mg, 82% recovery after flash chromatography).

Example 5

Control Reaction to Demonstrate Inertness of R$_f$CH$_2$NH— to Peptide Coupling Reactions

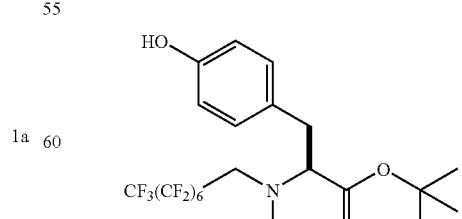

3c

A solution of Boc-Ala-OH (66 mg, 0.35 mmol), HBTU (118 mg, 0.31 mmol) and DIEA (90 µL, 0.52 mmol) in DMF (1.5 mL) was stirred for two minutes then transferred to a flask containing monofluoroalkyated compound 3c (60 mg, 0.087 mmol). TLC analysis showed only starting material ($R_f$=0.5 in hexanes/Et$_2$O 4/1). After 30 min, the reaction mixture was diluted with 30 mL of Et$_2$O and washed with 2×30 mL H$_2$O. The Et$_2$O was dried (MgSO$_4$) and the solvent evaporated. The residue thus obtained was filtered through silica gel using Et$_2$O:hexanes (1:3) to yield 54 mg (90% isolated after column chromatography) of unchanged 3c (NMR, TLC).

Example 6

Peptide Synthesis

P4, P5, & P6

Peptides were prepared using the N-Fluorenylmethoxycarbonyl (Fmoc) amino acid derivatives for Merrifield solid-phase synthesis (NovaGel Rink amide resin). N-α-Fmoc-α-S-amino acids were used with standard side chain protecting groups.

Two identical peptides were synthesized in parallel, either manually or in the synthesizer. One was F-capped and one was acetyl-capped to serve as control. Manual couplings were carried out using 4 eq Fmoc-amino acid, 3.6 eq HBtU, and 6 eq DIEA in DMF for 30 min. In case of a positive Kaiser test, the coupling was repeated. Deprotection was effected by 50% v/v piperidine in DMF (2×15 min).

Automated couplings were carried out in an Advanced ChemTech model 348 synthesizer. Each coupling used 7.5 eq Fmoc-amino acid, 7 eq HOBt, and 7 eq DIC in NMP for 30 min. Deprotection was effected by 50% vol/vol piperidine in NMP (2×10 min).

Incomplete couplings were generated as described below under Fluorous Capping Methods (Examples 8 and 9). Peptides were cleaved from the resin using TFA/triisopropyl silane (TIS)/water=95/2.5/2.5 or TFA/TIS/etanedithiol (EDT)/water=94/1/2.5/2.5 for 2-3 hours. The crude reaction mixture after cleavage and rotary-evaporation was treated with cold Et$_2$O. The precipitated peptides were sufficiently pure for HPLC and ESI analysis.

Example 7

Preparation and Characterization of Reagent 1b

[A] 1-(p-Toluensulfonyl)oxy-1H,1H-perfluorodecane: In a 250 mL round bottom flask, 1H,1H-perfluorodecanol (24.88 g, 49.8 mmol) and tosyl chloride (9.53 g, 49.6 mmol) were suspended in methylene chloride (150 mL). Triethylamine (7.25 mL, 52 mmol) and 4-dimethylaminopyridine (50 mg) were added and the reaction mixture was stirred for 12 hours at 22° C. The resulting white suspension was diluted to 350 mL with methylene chloride and extracted with water (3×100 mL). The organic phase was rotary-evaporated and dried in vacuum yielding 30.94 g (95%) of 1-(p-toluensulfonyl)oxy-1H,1H-perfluorodecane as a white powder. $^1$H NMR (CDCl$_3$, 300 MHz, ref TMS=0 ppm) 2.5 (s, 3H), 4.5 (t, 2H, J=18 Hz, CH$_2$), 7.4 (d, 2H), 7.8 (d, 1H).

[B] 1-Iodo-1H,1H-perfluorodecane: A solid mixture of the previous product (19.63 g, 30 mmol), KI (9.96 g, 60 mmol) and PEG 4000 (40 g) was liquefied by heating to 150° C. and stirred for 7 hours. The flask was allowed to cool, water (100 mL) was added, then the flask was fitted with a Dean-Stark trap and heating was resumed. The ensuing steam-distillation caused the product to collect in the bottom of the trap as a liquid that tended to solidify. After 2 hours the mostly solid collected product was melted by heating the trap with a heat gun. It formed a clear lower phase which was drained into a vial, where it resolidified soon. Yield of 1-iodo-1H,1H-perfluorodecane as a white powder was 9.02 g (14.78 mmol, 49%). $^1$H NMR (CDCl$_3$, 300 MHz, ref TMS=0 ppm) 3.6 (t, CH$_2$R$_f$).

The solid that remained in the cooled still was collected on a glass frit and thoroughly washed with water, then dried. NMR showed pure starting material. Recovery was 8.54 g (13.05 mmol), material balance 93%.

In a comparative experiment, 1-iodo-1H,1H-perfluorooctane was obtained by the same method in 73% yield. The recovered tosylate was 17%.

[C] (Bis-trifluoroacetoxy)iodo-1H,1H-perfluorodecane: This compound was obtained as described previously for (bis-trifluoroacetoxy)iodo-1H,1H-perfluorooctane. In a typical experiment, hydrogen peroxide (50% wt/wt, 1.4 mL, 24 mmol) was added dropwise into trifluoroacetic anhydride (TFAA) (40 mL) under magnetic stirring and cooling in an ice/salt bath. 1-Iodo-1H,1H-perfluorodecane (12.29 g, 20.1 mmol) was added rapidly, the cooling bath was removed, and the reaction was allowed to proceed under nitrogen for 16 hrs. The volatiles were removed under vacuum yielding 15.92 g of a white powder. Fresh TFAA (10 mL) was added, the mixture stirred 24 hrs, the volatiles removed to yield 15.947 g (95%) of product that was used directly to prepare iodonium salt 1b.

The product was added in one portion to (CF$_3$SO$_2$)$_2$NH (6.63 g, 23.6 mmol). The two solids were slurried in FC 72 (perfluorohexanes) and TFAA (3 mL). After 15 min benzene (2.25 mL, 25 mmol) was added in one portion and a clear solution resulted. The reaction mixture began to separate into two phases within 20 min; stirring was continued under nitrogen for 22 hrs at ambient temperature. Evaporation of the volatiles followed by stirring with ice/water produced a white precipitate. This was collected on a glass frit, dried in air, then under vacuum yielding 16.18 g (87%) of 1b as a white powder, which was used directly in capping reactions. $^1$H NMR (CDCl$_3$/CH$_3$CN=95/5, 300 MHz, ref. TMS=0 ppm) 4.8 (t, 2H, J=18 Hz, CH$_2$R$_f$), 7.6 (m, 2H), 7.8 (m, 1H), 8.1 (m, 2H).

Example 8

Fluorous Capping Method

Automated Synthesizer

The results of an Fmoc-coupling utilizing less than stoichiometric reagents were unpredictable, usually resulting in unrealistically high or inconsequentially low deletions. Thus, ca 20% deletions were deliberately generated as follows:

The parallel syntheses were stopped after a deprotection step. The two resins were removed from the synthesizer into tared scintillation vials, with the help of methylene chloride and ether, then the solvents were decanted and the resins were dried in vacuum for one hour. Twenty percent by weight of each resin was removed, the remainder returned to the synthesizer and swollen with DMF. The synthesis was resumed and one more coupling was carried out. The 20% portions of each resin were returned to the machine now. At this point each resin was presumed to be carrying 80% desired Fmoc-protected peptide, and 20% deletion, unprotected. The unprotected deletions were now capped with the following parallel protocol.

Step one: rinse the resins twice with CH$_2$Cl$_2$ to displace DMF, then in well A, add 3.5 mL of a solution of 1b (675 mg, 0.75 mmol) in CH$_2$Cl$_2$ (7 mL, containing 140 μL, 2% vol/vol, of DMF), and in well B, add 3.5 mL acetylation mixture (10 mL DMF, 0.6 mL Ac$_2$O, 0.1 mL DIEA); shake 3 min.

Step two: in well A, add 0.5 mL collidine solution (150 microL in 1.5 mL CH$_2$Cl$_2$), in well B, 0.5 mL acetylation mixture; shake 10 min; wash twice with CH$_2$Cl$_2$.

To ensure complete capping, the above protocol was repeated once more. Then the usual sequence of deprotection, washing, and coupling cycles was resumed to complete the peptide. To produce more than one intentional deletion, the above operations were repeated exactly at another position.

Example 9

Fluorous Capping Method

Manual Flow Method

Before starting the parallel manual synthesis, the two peptide vessels were tared.

After a deprotection step, the resins were rinsed well with CH$_2$Cl$_2$, then the loosely capped vessels were placed in a vacuum dessiccator for one hour. The amount of resin in each was determined by difference, then 20% was removed. One coupling step was carried out, then the 20% amounts of resins were returned to the respective vessels. After rinsing and swelling with 3×10 mL CH$_2$Cl$_2$ shake washes, the F-capping was conducted as follows:

Step one: the same solution of 1b as for the automated protocol was added into each vessel, with mild shaking for 3 min. Then the fluorous-capping solutions were drained into their original scintillation vials and reserved. If the recovered solution became cloudy because the resin had entrained some DMF, 10-20 μL DMF were added to redissolve all 1b.

Step two: into each vessel was added collidine (150 μL in 3 mL CH$_2$Cl$_2$) with mild shaking for 10 min. Then the resins were washed twice with CH$_2$Cl$_2$.

Step three: the above two steps were repeated using the recovered 1b solutions. (Recovered solutions that had been kept for days in the refrigerator could still be used successfully in F-capping).

Example 10

Control Experiments

Compatibility with Cys and Met Residues

The model compound Fmoc-Cys(Trt)OEt was prepared by stirring Fmoc-Cys(Trt)OH (146 mg, 0.25 mmol), EtI (25 microL, 0.3 mmol), and NaHCO$_3$ (85 mg, 1 mmol) in DMF (1 mL) for 18 hours. TLC showed one spot (R$_f$=0.8, Et$_2$O). Dilution with Et$_2$O (30 mL) and extraction with water (2×30 mL), drying and evaporation gave 140 mg (91%). $^1$H NMR (CD$_2$Cl$_2$, 300 MHz, ref. TMS=0 ppm) 1.1 (t, 3H, OCH$_2$CH$_3$), 4.0 (q, 2H, OCH$_2$CH$_3$), 4.2-4.3 (m, 3H, cysteine CH, CH$_2$), 5.1-5.2 (br, 3H, Fmoc CH, CH$_2$), 7.0-8.0 (m, 23H, aromatic H). NMR experiment: Fmoc-Cys(Trt)OEt (15 mg, 0.024 mmol) and 1a (21 mg, 0.024 mmol) were dissolved in CD$_2$Cl$_2$ (0.75 mL). After 2.5 hrs the NMR signals of were unchanged Fmoc-Cys(Trt)OEt. The baseline-separated signals of 1a at 4.8 (CH$_2$) and 8.0 (ortho-aromatic H) were also unchanged. Unknown products were visible after 30 hrs but the original signals seemed largely unchanged.

Similarly was prepared Fmoc-Met-OEt in 75% yield. $^1$H NMR (CD$_2$Cl$_2$, 300 MHz, ref. TMS=0 ppm) 1.1 (t, 3H, OCH$_2$CH$_3$), 2.0 (s, 3H, SCH3), 4.0 (q, 2H, OCH$_2$CH$_3$), 4.1-4.3 (m, 5H, methionine CH, CH$_2$, CH$_2$), 5.1-5.2 (br, 3H, Fmoc CH, CH$_2$), 7.2-7.8 (m, 8H, Fmoc aromatic). NMR experiment: Fmoc-Met-OEt (12 mg, 0.030 mmol) and C-8 (26 mg, 0.030 mmol) were dissolved in CD$_2$Cl$_2$ (0.75 mL). After 15 min the iodonium salt signals and nearly all the S—CH$_3$ singlet had disappeared. New signals at 3.1 (s) and 3.5-4.0 (br, unresolved) presumably were the methyl and R$_f$CH$_2$ groups of the fluoroalkyl sulfonium salt.

Example 11

Fluoroalkylation of H-Tyr-OBut with 1b

Into a solution of H-Tyr-OBut, (118 mg, 0.5 mmol) and iodonium salt 1b (483 mg, 0.5 mmol) in CH$_2$Cl$_2$ (7 mL), was added a solution of 2,4,6-collidine (73 μL, 0.55 mmol) CH$_2$Cl$_2$ (3 mL), were stirred at room temperature for 1 hour (by TLC the reaction seemed complete in 10 min). Dilution with CH$_2$Cl$_2$, extraction with 2×50 mL 0.1 M citric acid and evaporation, followed by chromatography (Et$_2$O/hexanes 1/1) gave 287 mg (80% yield) of C$_9$F$_{19}$CH$_2$TyrOBut as a white powder. $^1$H NMR (CDCl$_3$, 300 MHz, ref. TMS=0 ppm) 1.4 (s, 9H, But), 2.8 (m, 2H, tyrosine CH$_2$), 3.0-3.4 (ABX$_3$, m, 2H, R$_f$CF$_2$CH$_2$), 3.5 (t, 1H), 6.7 (d, 2H), 7.0 (d, 2H).

C$_9$F$_{19}$CH$_2$NH-Tyr-OBut (287 mg, 0.4 mmol), ethyl chloroformate (42 microL, 0.44 mmol) and triethylamine (70 μL, 0.5 mmol) were stirred in CH$_2$Cl$_2$ (5 mL) at room temperature for 1 hr. The mixture was diluted with CH$_2$Cl$_2$ (30 ml), extracted with 2×30 mL 0.1 M citric acid. The organic phase was dried and evaporated to yield 286 mg (92%) of the desired C$_9$F$_{19}$CH$_2$NH-Tyr(OCOEt)-OBut, pure by NMR. $^1$H NMR (CDCl$_3$, 300 MHz, ref. TMS=0 ppm) 1.4 (overlapping s, 9H, But and t, 3H, OCH$_2$CH$_3$), 2.8 (m, 2H, tyrosine CH$_2$), 3.0-3.4 (ABX$_3$, m, 2H, R$_f$CF$_2$CH$_2$), 3.4 (t, 1H), 4.3 (q, 2H, OCH$_2$CH$_3$), 6.7 (d, 2H), 7.0 (d, 2H).

Example 12

Inertness of C$_9$F$_{19}$CH$_2$NH— to Fmoc-Peptide Manual Coupling Conditions

A solution of Fmoc-Ala-OH (102 mg, 0.33 mmol), HBTU (112 mg, 0.3 mmol) and DIEA (85 μL, 0.5 mmol) in DMF (2 mL) was stirred for two minutes then transferred into a flask containing C$_9$F$_{19}$CH$_2$NH-Tyr(OCOEt)-OBut (64 mg, 0.083 mmol). After 3 hrs, the reaction mixture was reduced to small volume and the residue was directly filtered through silica gel using hexanes:Et$_2$O (2:1) to yield unchanged C$_9$F$_{19}$CH$_2$NH-Tyr(OCOEt)-OBut (NMR, TLC) quantitatively.

Example 13

Inertness of R$_f$CH$_2$NH— to Fmoc-Peptide Deprotection Conditions

The larger model compound C$_7$F$_{15}$CH$_2$NH-Phe-Ala-(2-methyl)benzyl amide, easier to isolate from a piperidine and DMF-containing mixture, was prepared as follows:

A solution of Boc-Ala-OH (946 mg, 5 mmol), HBTU (1.89 g, 5 mmol) and DIEA (1.72 mL, 10 mmol) in DMF (10 mL) was stirred for 5 minutes, then (2-methyl)benzyl amine (640 μL, 5 mmol) was added in one portion. After 3 hours the mixture was diluted with 75 mL CH$_2$Cl$_2$, extracted with 0.1 M citric acid (100 mL) and water (6×100 mL). Rotary evaporation afforded 1.365 g (93% of theory) of Boc-Ala-(2-methyl)benzyl amide as a white powder that was used directly in the next step. Trifluoroacetic acid (50% in CH$_2$Cl$_2$, 6 mL) was added and the solution stirred 2 hours. Rotary evaporation and pumping in vacuum for 3 hours gave the crude trifluoroacetate salt of H-Ala-(2-methyl)benzyl amide as an oil, which was used directly. This oil was dissolved in DMF (5 mL) and DIEA was added dropwise until the solution was neutral to litmus. Separately, Boc-Phe-OH (1.234 g, 4.65 mmol) HBtU (1.764 g, 4.65 mmol) and DIEA (1.6 mL, 9.3 mmol) were stirred for 5 min in DMF (5 mL), then added into the solution of H-Ala-(2-methyl)benzyl amide. After 3 hours workup as above with citric acid and water gave 2.23 g of crude material that was dissolved in the minimum amount of $CH_2Cl_2$ and stored at $-20°$ C. overnight. The resulting precipitate was triturated with pentane, filtered and dried to yield 1.349 g (66%) of Boc-Phe-Ala-(2-methyl)benzyl amide. $^1$H NMR ($CDCl_3$, 300 MHz, ref TMS=0 ppm) 1.3-1.5 (15H, two d, s, Me, Me, But), 3.0-3.1 (m, 2H, $PhCH_2$), 4.3 (1H, br, NH), 4.4 (1H, m, PhCH), 4.9 (1H, br, NH), 5.0 (1H, m, CH), 6.5 (1H, d, CH), 6.7 (1H, br, NH), 7.1-7.4 (10H, Ph rings).

This product (220 mg, 0.5 mmol) was stirred with trifluoroacetic acid (50% in $CH_2Cl_2$, 3 mL) for one hr, then evaporated to give the crude trifluoroacetate of H-Phe-Ala-(2-methyl)benzyl amide. This was dissolved in $CH_2Cl_2$ (5 mL) and 0.5 M $NaHCO_3$ was added with stirring until the aqueous phase was basic to litmus (ca 3 mL), then 2 mL more were added, followed by iodonium salt 1b (434 mg, 0.5 mmol). The biphasic mixture was stirred rapidly at rt for 1.5 hrs, at which point TLC confirmed a complete reaction. The reaction was diluted with $CH_2Cl_2$ (50 mL), extracted with $NaHCO_3$ (50 mL), 0.1 M citric acid (50 mL). The organic phase was dried and evaporated to an oil that soon solidified. Pumping in vacuum gave 310 mg (86%) of $C_7F_{15}CH_2NH$-Phe-Ala-(2-methyl)benzyl amide as a white powder. $^1$H NMR ($CDCl_3$, 300 MHz, ref TMS=0 ppm) 1.3 and 1.5 (9H, two d, Me, Me), 2.8 and 3.5 (2H, two m, $PhCH_2$), 3.2 (2H, $ABX_3$, $R_fCH_2$), 4.5 (1H, m, PhCH), 5.1 (1H, m, CH), 6.6 (1H, d, CH), 7.5 (1H, br, NH), 7.2-7.4 (10H, Ph rings).

Part of this product (295 mg) was dissolved in piperidine (50% vol/vol in DMF, 2 mL) and stirred for 20 hrs at rt. The reaction mixture was diluted with 75 mL of $Et_2O$ and washed with 3×50 mL 0.1 M citric acid. TLC analysis showed only starting material ($R_f$=0.6 in $Et_2O$). The $Et_2O$ was dried ($MgSO_4$) and evaporated. The product thus obtained (269 mg, 91%) was unchanged starting material by NMR analysis.

Example 14

Mass Spectrometry (ESI-MS) of P4, P5, & P6

ESI-MS Conditions: Finnigan LTQ, Thermo Electron Corp.; solutions were ~100 nM in MeOH/5% HCOOH unless otherwise noted, flow rate: 5 µL/min, spray voltage: 5 kV, capillary voltage: 40 V. Sample identities: (1) crude peptide; and (2) fragment isolated by HPLC. ESI in negative ion mode; peptide dissolved in $CH_3CN/0.1\%$ $NH_4OH$. An Ac indicates capped with $Ac_2O$; $R_f$ indicates $-CH_2(CF_2)_8CF_3$; and an asterisk indicates positions where the peptide coupling was incomplete.

TABLE 4

Peptide P4 (Ac—NH—V*EAAIDYIDA-$CONH_2$)

| Fragment | $MW_{calc}$ (Da) | $MW_{obsd}$ (Da) | Sample |
|---|---|---|---|
| $H_2N$—VEAAIDYIDA-$CONH_2$ | 1061.55 | 1062.45 | 1 |
| Ac—NH-EAAIDYIDA-$CONH_2$ | 1004.49 | 1005.32; 1027.52 (+Na) | 1 |
| $H_2N$—VEAAIDYIDA-$CONH_2$ | 1061.55 | 1062.46 | 1 |

TABLE 4-continued

Peptide P4 (Ac—NH—V*EAAIDYIDA-$CONH_2$)

| Fragment | $MW_{calc}$ (Da) | $MW_{obsd}$ (Da) | Sample |
|---|---|---|---|
| $R_fCH_2$—NH-EAAIDYIDA-$CONH_2$ | 1444.45 | 1445.16 (+Na) | 1 |

TABLE 5

Peptide P5 (Ac—NH—PT*GY*GSSSRRAPET-$CONH_2$)

| Fragment | $MW_{calc}$ (Da) | $MW_{obsd}$ (Da) | Sample |
|---|---|---|---|
| $H_2N$—PTGYGSSSRRAPET-$CONH_2$ | 1463.57 | 1464.58 | 1, 2 |
| Ac—NH-GYGSSSRRAPET-$CONH_2$ | 1307.62 | 1308.54 | 1, 2 |
| Ac—NH-GSSSRRAPET-$CONH_2$ | 1087.55 | 1088.42 | 1, 2 |
| $H_2N$—PTGYGSSSRRAPET-$CONH_2$ | 1463.57 | 1464.50 | 1, 2 |
| $R_fCH_2$—NH-GYGSSSRRAPET-$CONH_2$ | 1747.58 | 1748.33 | 1, 2 |
| $R_fCH_2$—NH-GSSSRRAPET-$CONH_2$ | 1527.50 | 1528.26 | 1, 2 |

TABLE 6

Peptide P6 (Ac—NH-GN*QW*AVGHLC—$CONH_2$)

| Fragment | $MW_{calc}$ (Da) | $MW_{obsd}$ (Da) | Sample |
|---|---|---|---|
| $H_2N$-GNQWAVGHLC—$CONH_2$ | 1082.50 | 1083.38 | 1, 2 |
| Ac—NH-QWAVGHLC—$CONH_2$ | 953.45 | 954.39 | 1, 2 |
| Ac—NH-AVGHLC—$CONH_2$ | 639.21 | 640.37 | 1, 2 |
| $H_2N$-GNQWAVGHLC—$CONH_2$ | 1082.50 | 1083.40 | 1 |
| $R_fCH_2$—NH-QWAVGHLC—$CONH_2$ | 1393.42 | 1394.27 | 1 |
| $R_fCH_2$—NH-AVGHLC—$CONH_2$ | 1079.28 | 1080.24 | 1 |

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound represented by formula I:

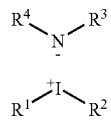

I wherein $R^1$ is represented by formula

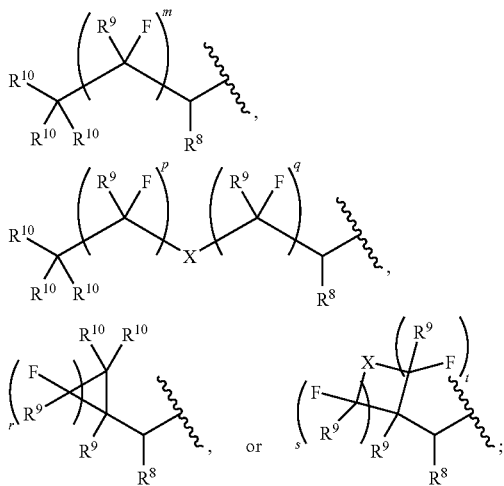

wherein $R^8$ is H, alkyl, or fluoroalkyl; $R^9$ is H, F, alkyl, or fluoroalkyl; $R^{10}$ is H or F; X is O, $NR^5$, or S; m is 1-18 inclusive; p is 0-10 inclusive; q is 1-10 inclusive; r is 1, 2, 3, 4, 5, 6, 7, or 8; s is 1, 2, 3, 4, 5, or 6; and t is 0, 1, 2, 3, 4, 5, or 6;

$R^2$ is aryl, heteroaryl, alkenyl, or alkynyl;

$R^3$ and $R^4$ represent independently for each occurrence —$SO_2R^5$, —$C(O)R^5$, —$CO_2R^5$, —$C(O)N(R^6)_2$, —$C(S)R^5$, —$C(S)OR^5$, —$C(S)N(R^6)_2$, or -aryl-$(R^7)_n$;

$R^5$ represents independently for each occurrence alkyl, fluoroalkyl, chloroalkyl, alkenyl, aryl, or aralkyl;

$R^6$ represents independently for each occurrence H, alkyl, fluoroalkyl, chloroalkyl, aryl, or aralkyl;

$R^7$ represents independently for each occurrence nitro, cyano, halogen, —$SO_2R^5$, —$C(O)R^5$, —$CO_2R^5$, or —$C(O)N(R^6)_2$; and n is independently 0, 1, 2, 3, 4, or 5 in accord with the rules of valence.

2. The compound of claim 1, wherein $R^1$ is represented by formula:

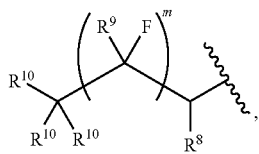

wherein $R^8$ is H, alkyl, or fluoroalkyl; $R^9$ is H, F, alkyl, or fluoroalkyl; $R^{10}$ is H or F; and m is 1-18 inclusive.

3. The compound of claim 1, wherein $R^1$ is represented by formula:

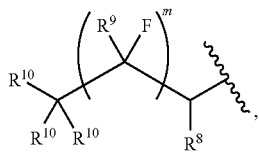

wherein $R^8$ is H; $R^9$ is H or F; $R^{10}$ is H or F; and m is 3-10 inclusive.

4. The compound of claim 1, wherein $R^1$ is —$CH_2(CF_2)_m CF_3$ and m is 3-10 inclusive.

5. The compound of claim 1, wherein $R^1$ is —$CH_2(CF_2)_6 CF_3$.

6. The compound of claim 1, wherein $R^1$ is —$CH_2(CF_2)_8 CF_3$.

7. The compound of claim 1, wherein $R^2$ is aryl.

8. The compound of claim 1, wherein $R^2$ is optionally substituted phenyl.

9. The compound of claim 1, wherein $R^2$ is phenyl.

10. The compound of claim 1, wherein $R^3$ and $R^4$ represent independently for each occurrence —$SO_2R^5$, —$C(O)R^5$, or —$CO_2R^5$.

11. The compound of claim 1, wherein $R^3$ and $R^4$ represent independently for each occurrence —$SO_2R^5$.

12. The compound of claim 1, wherein $R^3$ and $R^4$ represent independently for each occurrence —$SO_2R^5$, and $R^5$ is alkyl or fluoroalkyl.

13. The compound of claim 1, wherein $R^3$ and $R^4$ are —$SO_2CF_3$.

14. The compound of claim 1, wherein $R^1$ is —$CH_2(CF_2)_6 CF_3$ and $R^2$ is phenyl.

15. The compound of claim 1, wherein $R^1$ is —$CH_2(CF_2)_8 CF_3$ and $R^2$ is phenyl.

16. The compound of claim 1, wherein $R^1$ is —$CH_2(CF_2)_6 CF_3$; $R^2$ is phenyl; and $R^3$ and $R^4$ are —$SO_2CF_3$.

17. The compound of claim 1, wherein $R^1$ is —$CH_2(CF_2)_8 CF_3$; $R^2$ is phenyl; and $R^1$ and $R^4$ are —$SO_2CF_3$.

18. A method of preparing a fluorocarbon compound, comprising the step of:
treating a compound comprising a nucleophilic functional group with a trivalent iodonium compound to generate a fluorocarbon compound, wherein said trivalent iodonium compound is represented by formula I:

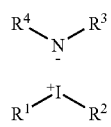

wherein
$R^1$ represented by formula

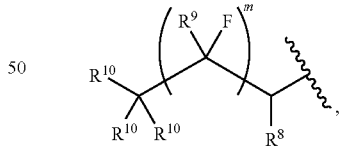
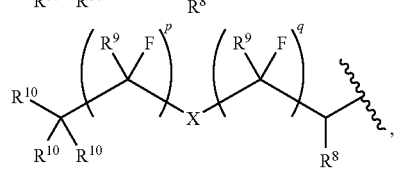
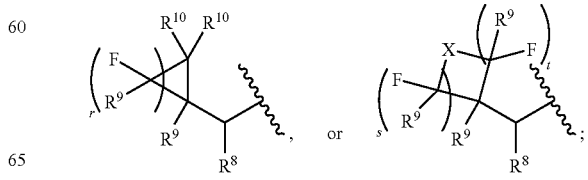

wherein R⁸ is H, alkyl, or fluoroalkyl; R⁹ is H, F, alkyl, or fluoroalkyl; R¹⁰ is H or F; X is O, NR⁵, or S; m is 1-18 inclusive; p is 0-10 inclusive; q is 1-10 inclusive; r is 1, 2, 3, 4, 5, 6, 7, or 8; s is 1, 2, 3, 4, 5, or 6; and t is 0, 1, 2, 3, 4, 5, or 6;

R² is aryl, heteroaryl, alkenyl, or alkynyl;

R³ and R⁴ represent independently for each occurrence —SO₂R⁵, —C(O)R⁵, —CO₂R⁵, —C(O)N(R⁶)₂, —C(S)R⁵, —C(S)OR⁵, —C(S)N(R⁶)₂, or -aryl-(R⁷)ₙ;

R⁵ represents independently for each occurrence alkyl, fluoroalkyl, chloroalkyl, aryl, or aralkyl;

R⁶ represents independently for each occurrence H, alkyl, fluoroalkyl, chloroalkyl, aryl, or aralkyl;

R⁷ represents independently for each occurrence nitro, cyano, halogen, —SO₂R⁵, —C(O)R⁵, —CO₂R⁵, or —C(O)N(R⁶)₂; and n is independently 0, 1, 2, 3, 4, or 5 in accord with the rules of valence.

19. A compound represented by formula I:

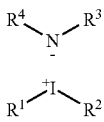

I wherein

R¹ is fluoroheteroalkyl, fluorocycloalkyl, fluoroheterocycloalkyl, fluorocycloalkyl(C₁-C₆)alkyl, fluoroheterocycloalkyl(C₁-C₆)alkyl, (fluoroalkyl)aralkyl, fluoroaralkyl, or fluoroalkenyl(C₁-C₆)alkyl;

R² is aryl, heteroaryl, alkenyl, or alkynyl;

R³ and R⁴ represent independently for each occurrence —SO₂R⁵, —C(O)R⁵, —CO₂R⁵, —C(O)N(R⁶)₂, —C(S)R⁵, —C(S)OR⁵, —C(S)N(R⁶)₂, or -aryl-(R⁷)ₙ;

R⁵ represents independently for each occurrence alkyl, fluoroalkyl, chloroalkyl, alkenyl, aryl, or aralkyl;

R⁶ represents independently for each occurrence H, alkyl, fluoroalkyl, chloroalkyl, aryl, or aralkyl;

R⁷ represents independently for each occurrence nitro, cyano, halogen, —SO₂R⁵, —C(O)R⁵, —CO₂R⁵, or —C(O)N(R⁶)₂; and n is independently 0, 1, 2, 3, 4, or 5 in accord with the rules of valence.

20. The compound of claim 19, wherein R¹ is fluoroheteroalkyl, fluorocycloalkyl(C₁-C₆)alkyl, fluoroheterocycloalkyl(C₁-C₆)alkyl, or fluoroaralkyl.

21. The compound of claim 19, wherein R¹ is fluorocycloalkyl(C₁-C₆)alkyl.

22. A method of preparing a fluorocarbon compound, comprising the step of:

treating a compound comprising a nucleophilic functional group with a trivalent iodonium compound to generate a fluorocarbon compound, wherein said trivalent iodonium compound is represented by formula I:

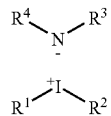

I wherein

R¹ is fluoroheteroalkyl, fluorocycloalkyl, fluoroheterocycloalkyl, fluorocycloalkyl(C₁-C6)alkyl, fluoroheterocycloalkyl(C₁-C₆)alkyl, (fluoroalkyl)aralkyl, fluoroaralkyl, or fluoroalkenyl(C₁-C₆)alkyl;

R² is aryl, heteroaryl, alkenyl, or alkynyl;

R³ and R⁴ represent independently for each occurrence —SO₂R⁵, —C(O)R⁵, —CO₂R⁵, —C(O)N(R⁶)₂, —C(S)R⁵, —C(S)OR⁵, —C(S)N(R⁶)₂, or -aryl-(R⁷)ₙ;

R⁵ represents independently for each occurrence alkyl, fluoroalkyl, chloroalkyl, aryl, or aralkyl;

R⁶ represents independently for each occurrence H, alkyl, fluoroalkyl, chloroalkyl, aryl, or aralkyl;

R⁷ represents independently for each occurrence nitro, cyano, halogen, —SO₂R⁵, —C(O)R⁵, —CO₂R⁵, or —C(O)N(R⁶)₂; and n is independently 0, 1, 2, 3, 4, or 5 in accord with the rules of valence.

* * * * *